United States Patent
Sarasa Barrio

(10) Patent No.: US 9,255,932 B2
(45) Date of Patent: Feb. 9, 2016

(54) ANTIBODY, KIT AND METHOD FOR DETERMINING AMYLOID PEPTIDES

(75) Inventor: Manuel Sarasa Barrio, Saragossa (ES)

(73) Assignee: Aracion Biotech, S.L., Zaragoza (ES)

(*) Notice: Subject to any disclaimer, the term of this patent is extended or adjusted under 35 U.S.C. 154(b) by 127 days.

(21) Appl. No.: 14/004,634

(22) PCT Filed: Apr. 3, 2012

(86) PCT No.: PCT/ES2012/070231
§ 371 (c)(1),
(2), (4) Date: Sep. 11, 2013

(87) PCT Pub. No.: WO2012/140296
PCT Pub. Date: Oct. 18, 2012

(65) Prior Publication Data
US 2014/0024054 A1 Jan. 23, 2014

(30) Foreign Application Priority Data
Apr. 12, 2011 (EP) .................... 11382107

(51) Int. Cl.
*G01N 33/68* (2006.01)
*A61K 39/395* (2006.01)
*C07K 16/18* (2006.01)

(52) U.S. Cl.
CPC ............ *G01N 33/6896* (2013.01); *C07K 16/18* (2013.01); *C07K 2317/34* (2013.01); *G01N 2333/4709* (2013.01); *G01N 2800/2821* (2013.01); *G01N 2800/56* (2013.01)

(58) Field of Classification Search
None
See application file for complete search history.

(56) References Cited

U.S. PATENT DOCUMENTS

| 2004/0248197 | A1 | 12/2004 | Holtzman |
| 2008/0199879 | A1 | 8/2008 | Takayama |
| 2009/0035790 | A1 | 2/2009 | SarasaBarrio |

FOREIGN PATENT DOCUMENTS

| CN | 101861521 | | 10/2010 |
| EP | 0683234 | A1 | 11/1995 |
| EP | 1480041 | A1 | 11/2004 |
| EP | 1717250 | A1 | 11/2006 |
| EP | 1881008 | A1 | 1/2008 |
| EP | 2275814 | A1 | 1/2011 |
| WO | 9012871 | | 11/1990 |
| WO | 0162801 | | 8/2001 |
| WO | 0246237 | | 6/2002 |
| WO | 03015617 | | 2/2003 |
| WO | WO 03039467 | A2 | 5/2003 |
| WO | WO 2004013172 | A2 | 2/2004 |
| WO | WO 2004029630 | A1 | 4/2004 |
| WO | 2006046644 | | 5/2006 |
| WO | 2006053251 | | 5/2006 |
| WO | 2007022015 | | 2/2007 |
| WO | 2007050359 | | 5/2007 |
| WO | 2007140843 | | 12/2007 |
| WO | WO 2009015696 | A1 | 2/2009 |

OTHER PUBLICATIONS

Rossi M. et al., "Immunogenic, antigenic, fibrillogenic and inflammatory properties of new simplified b-amyloid peptides" Molecular Immunology (2009), 46(13), pp. 2524-2532.
Saito Takanomi C; et al "Amino- and carboxyl-terminal heterogeneity of beta-amyloid peptides deposited in human brain" Neuroscience Letters (1996), vol. 215, n° 3, pp. 173-176.
Bacher et al, Neuroscience Letters, vol. 449, No. 3, Jan. 16, 2009, pp. 240-245.
European Search Report mailed Mar. 2, 2015 for European Application No. 12771472.3.
Fukomoto et al., Arch. Neurol. Jul. 2003, vol. 60, pp. 958-964.
Grundman et al., Arch. Neurol., Jan. 2004, vol. 61, No. 1, pp. 59-66.
Lambert et al, Neurology, vol. 73, No. 11, Sep. 2009, pp. 847-853.
Mayeux et al., Ann Neurol. 1999, vol. 46, pp. 412-416.
McKhann et al., Neurology, Jul. 1984, vol. 34, pp. 939-944.
Mehta et al., Arch. Neurol., Jan. 2000, vol. 57, pp. 100-105.
Morris et al., Arch. Neurol., Mar. 2001, vol. 58, No. 3, pp. 397-405.
Perdivara et al, Analytical And Bioanalytical Chemistry, vol. 391, No. 1, Mar. 28, 2008, pp. 325-336.
Petersen et al., Arch. Neurol., Mar. 1999, vol. 56, No. 3, pp. 303-308.
Tabert et al., Arch. Gen. Psychiatry, Aug. 2006, vol. 63, No. 8, pp. 916-924.
Thal et al., Acta Neuropathol, Dec. 2000, vol. 100, No. 6, pp. 608-617, abstract only.
Waterhouse et al., Nucl. Acids. Res., 1993, vol. 21, No. 9, pp. 2265-2266.
Written Opinion of the International Searching Authority mailed Jul. 24, 2012 in International Application No. PCT/ES2012/070231.
Zetterberg, Recent Patents on CNS Drug Discovery, vol. 3, No. 2, Jun. 1, 2008, pp. 109-111.
International Search Report dated Jul. 24, 2012 in corresponding PCT Application No. PCT/ES2012/070231, filed Apr. 3, 2012.

*Primary Examiner* — Gregory S Emch
(74) *Attorney, Agent, or Firm* — RatnerPrestia

(57) ABSTRACT

The invention relates to the field of immunoassays which allow the detection of Aβ17 peptides by virtue of the use of an anti-Aβ17 antibody and a kit and method using said antibody. The invention also relates to a method for diagnosing or distinguishing between different stages of a neurodegenerative disease.

8 Claims, 8 Drawing Sheets

(A)

| | FP 17 | TP 17 | CB 17 | TP+CB 17 | TP17+TP40+TP42 | CB17+CB40+CB42 | PIB (17+40+42) |
|---|---|---|---|---|---|---|---|
| CS>65 | 23.59 ± 17.54 | 71.59 ± 52.06 | 79.25 ± 47.64 | 150.84 ± 98.70 | 197.91 ± 54.49 | 262.43 ± 65.16 | 460.35 ± 109.44 |
| MCI possible | 33.42 ± 53.09 | 80.91 ± 77.84 | 71.89 ± 35.42 | 152.90 ± 110.29 | 224.53 ± 108.02 | 240.99 ± 69.81 | 465.52 ± 158.57 |
| MCI probable | 21.30 ± 6.87 | 57.22 ± 24.53 | 63.60 ± 19.40 | 120.80 ± 41.92 | 212.75 ± 88.12 | 306.03 ± 78.21 | 518.78 ± 132.62 |
| AD mild | 29.98 ± 17.93 | 74.97 ± 54.72 | 72.07 ± 30.41 | 147.04 ± 83.85 | 221.93 ± 62.19 | 310.04 ± 81.29 | 531.97 ± 107.38 |

| | TP40 | CB40 | TP42 | CB42 |
|---|---|---|---|---|
| CS>65 | 87.0 ± 11.3 | 62.3±8.3 | 39.5±10.9 | 59.5±44.8 |
| MCI possible | 89.2±16.7 | 52.5±6.4 | 54.4±40.5 | 46.7±47.9 |
| MCI probable | 99.6±18.2 | 58.5±18.9 | 56.0±56.0 | 41.2±74.7 |
| AD mild | 91.4±18.9 | 65.9±13.9 | 55.6±28.2 | 48.4±83.3 |

Fig. 3

ANTIBODY, KIT AND METHOD FOR DETERMINING AMYLOID PEPTIDES

CROSS REFERENCE TO RELATED APPLICATIONS

This application is a U.S. National Stage pursuant to 35 U.S.C. §371 of International Patent Application No. PCT/ES2012/070231, filed Apr. 3, 2012, which claims priority to European Patent Application No. 11382107.8, filed Apr. 12, 2011, both of which are incorporated herein by reference in their entireties for all purposes.

TECHNICAL FIELD

The invention relates to the field of immunoassays which allow the detection of Aβ17 peptides by virtue of the use of an anti-Aβ17 antibody and a kit and method using said antibody. The invention also relates to a method for diagnosing or distinguishing between different stages of a neurodegenerative disease.

BACKGROUND OF THE INVENTION

Alzheimer's disease (AD) is a progressive degenerative disease of the central nervous system characterized by progressive and increasing memory loss, followed by loss of control of limbs and bodily functions with a fatal ending. It is by far the most common cause of dementia affecting 1 to 6% of people over the age of 65 years and between 10 to 20% of those over 80.

AD is distinguished from other types of dementia by several pathological features, including the progressive appearance in the brain of the patients of senile plaques in the extracellular space between neurons. The plaques have central cores of amyloid deposits formed mainly by fibrils of a 40-42 amino acids peptide referred to β amyloid peptide (Aβ) surrounded by degenerated neurites and glial cells. This peptide results from the proteolytic processing of a precursor protein called β amyloid precursor protein (βAPP).

The National Institute of Neurological and Communicative Disorders and Stroke (NINCDS) and the Alzheimer's Disease and Related Disorders Association (ADRDA) established the most commonly used NINCDS-ADRDA Alzheimer's Criteria for diagnosis in 1984. According to the NINCDS/ADRDA. These criteria are the following:

Definitive Alzheimer's disease: The patient meets the criteria for probable Alzheimer's disease and shows histopathologic evidence of AD via autopsy or biopsy.

Probable or prodromal Alzheimer's disease: Dementia has been established by clinical and neuropsychological examination. Cognitive impairments also have to be progressive and be present in two or more areas of cognition. The onset of the deficits has been between the ages of 40 and 90 years and finally there must be an absence of other diseases capable of producing a dementia syndrome.

Possible or non-prodromal Alzheimer's disease: There is a dementia syndrome with an atypical onset, presentation or progression; and without a known etiology; but no co-morbid diseases capable of producing dementia are believed to be in the origin of it.

Unlikely Alzheimer's disease: The patient presents a dementia syndrome with a sudden onset, focal neurologic signs, or seizures or gait disturbance early in the course of the illness.

Mild cognitive impairment (MCI, also known as incipient dementia, or isolated memory impairment) is a diagnosis given to individuals who have cognitive impairments beyond that expected for their age and education, but that do not interfere significantly with their daily activities (Petersen R C et al. (1999) Arch. Neurol. 56 (3): 303-8). It is considered to be the boundary or transitional stage between normal aging and dementia. Although MCI can present with a variety of symptoms, when memory loss is the predominant symptom it is termed "amnestic MCI" and is frequently seen as a risk factor for Alzheimer's disease (Grundman M et al. (2004). Arch. Neurol. 61 (1): 59-66). Studies suggest that these individuals tend to progress to probable or prodromal Alzheimer's disease at a rate of approximately 10% to 15% per year (Grundman M et at ad supra.) Additionally, when individuals have impairments in domains other than memory it is classified as non-amnestic single- or multiple-domain MCI and these individuals are believed to be more likely to convert to other dementias (Tabert M H et al. (2006). Arch. Gen. Psychiatry 63 (8): 916-24).

The diagnosis of MCI requires considerable clinical judgement, and as such a comprehensive clinical assessment including clinical observation, neuroimaging, blood tests and neuropsychological testing are best in order to rule out an alternate diagnosis. A similar assessment is usually done for diagnosis of Alzheimer's disease. MCI is diagnosed when there is (Morris J C et al. (2001). Arch. Neurol. 58 (3): 397-405):

Evidence of memory impairment
Preservation of general cognitive and functional abilities
Absence of diagnosed dementia In the last decade, several attempts have been performed to identify peripheral markers by using plasma, serum or circulating cells. In particular, because amyloid plaques are a defining feature of Alzheimer disease neuropathology, and Aβ can be detected in plasma, its measure is a compelling candidate biomarker for Alzheimer disease.

In clinical praxis, diagnosis of AD is carried out using clinical criteria based on the presence of typical clinical hallmarks and the exclusion of other types of dementia using neuroimaging techniques and blood analysis. Using these criteria, diagnostic reliability is acceptable although, according to studies done using brain autopsy, between 10-20% of the patients diagnosed with AD suffered from a different disease. Moreover, the current diagnostic methods can only be carried out when the neurodegenerative process is so advanced that the patient suffers from severe dementia and the brain damages are so extensive that the number of therapeutic measures is limited. Definitive diagnosis requires pathologic examination of post-mortem brain tissue.

In view of the fact that Aβ accumulates in the brain of AD patients and is a central element in the pathogenesis of AD, this protein has been considered as the most suitable candidate as AD biomarker. However, the use of Aβ as plasma biomarker for AD faces the problem that the concentrations of the Aβ peptides (Aβ(1-40) and Aβ(1-42)) in serum are extremely low, so that there are no assays which are sensitive enough so as to allow reliable detection of said peptide species.

Many different assays have been used to determine levels of amyloid beta peptides in biological samples (see e.g. the methods described by Scheuner et al (Nature Med., 1996, 2:864-870); Tamaoka A et al. (J Neurol Sci., 1996, 141, 65-68); Suzuki, N. et al. (Science, 1994, 264:1336-1340); WO200722015, Vanderstichele H et al. (Amyloid, 2000, 7, 245-258); Fukomoto y col. (Arch. Neurol. 2003, 60, 958-964); Mehta et al. (Arch. Neurol. 57, 2000, 100-105); Mayeux, R. et al. (Ann Neurol. 1999, 46, 412-416); Lanz, T. A and Schacthter, J. B. (J. Neuroscience Methods, 2006, 157:71-81), WO200750359, WO0162801, WO0315617, WO0246237, WO0413172. However, all the ELISA-based assays known to date have a lower detection limit which is not in the range of single digit pg/mL at the most, which is sufficient for detecting Aβ40 and Aβ42 in CSF as well as for detecting said species in plasma in patients suffering from familiar AD, but are unsuitable for detecting Aβ42 in the plasma of patients suffering from sporadic AD, wherein the Aβ42 plasma concentration is much lower.

To date, the only Aβ peptide assays showing a lower detection limit lower than the single digit pg/mL correspond to the assays described in WO200646644 and in WO2009015696.

WO200646644 describes an electrochemiluminiscent (ECL) sandwich assay wherein the mAb 21F12 (which recognises amino acids 33-42 of Aβ42) is coupled to magnetic beads, which are then used to capture the Aβ42 peptide in the sample containing Aβ42 and further contacted with 3D6 mAb coupled to a ruthenium complex. The amount of 3D6 antibody bound is then detected by the luminescence emitted by the ruthenium complex when electrical energy is applied. Using this assay, the inventors are capable of detecting as low as 0.5 pg/mL of a Aβ42 standard. However, when the same assay is used to compare Aβ42 in plasma samples from AD patients and healthy controls, no significant differences could be observed between the two sets of patients, which led the inventors to conclude that the amount of intact Aβ42 in serum is very low due to degradation and turned to a competitive ELISA assay using 21F12 mAb which provides lower sensitivity levels in the range of ng/mL.

WO2009015696 describes a high-sensitivity ELISA sandwich assay wherein the detection antibody is contacted with a biotin-labeled reagent showing specificity for said antibody. The reagent is contacted with streptavidin which is coupled to peroxidase. Peroxidase activity is then detected by colorimetry using TMB or fluorescently using QuantaBlue.

WO2006053251 describes a method for the determination of amyloid beta peptide species in a sample comprising contacting a sample with a denaturing agent, extracting the peptide pool from the sample-denaturing agent mixture, separating the amyloid beta peptide species from the pool and determining the amount of amyloid beta peptide species. This method requires a step of separation of the peptides prior to the determination, which results in increased processing time and increased costs.

Methods are known in the prior art to diagnose AD by detecting the levels of biomarkers present in the brain or CSF of patients. Different biomarkers have been characterised whose determination is carried out in CSF. CSF reflects directly the composition of the extracellular space of the central nervous system and thus, provides higher concentrations as biomarkers. However, CSF can only be retrieved by means of lumbar punction, which is not a routine diagnostic method easily accepted by patients suffering from dementia, let alone in patients with memory disorders. Thus, there is a need for AD biomarkers which can be detected in samples which can be non-invasively retrieved from the body.

Suitable AD biomarkers described in the prior art and which can be detected in plasma include (i) markers derived from the amyloid plaque, (ii) autoantibodies against Aβ or βAPP, (iii) inflammatory markers such IL-6, its receptor or gp130, C-reactive protein or oxidative stress (isoprostanes), (iv) markers of lipidic metabolism (apoE, oxysterols) and (v) vascular disease markers (homocysteine, lipoprotein b C1q) (Scheuner D et al. (1996) Nature Med 2, 864-870).

However, in view of the fact that Aβ accumulates in the brain of AD patients and is a central element in the pathogenesis of AD, this protein has been considered as the most suitable candidate as AD biomarker. However, the use of Aβ as plasma biomarker for AD faces the problem that the concentrations of the Aβ peptides (Aβ(1-40) and Aβ(1-42)) in serum are extremely low, so that there are no assays which are sensitive enough so as to allow reliable detection of said peptide species.

Furthermore, several antibodies have been described to detect Aβ peptides and to be used in immunological assays. For example, the monoclonal anti-Aβ(1-17) (6E10) is an antibody directed to the N-terminal region of the Aβ peptide, generated against the peptide Aβ(1-17) (Kim K S, et al. Neurosci. Res. Comm. 7; 1988) and recognizing the Aβ peptides including said region or the monoclonal antibody generated against the peptide Aβ(1-28) (Pierce).

However, there is a need in the art for improved immunological assays and kits to detect Aβ-derived peptides which overcome the problems of the methods and kits known in the art, in particular, which are sensitive enough to detect Aβ peptides in a reliable manner in plasma of patients suffering from sporadic AD. There is also a need for identifying biomarkers for the early diagnosis of AD which are sensitive and specific and which allow distinguishing cognitive impairment due to age from those associated with the early symptoms of the process, as well as to distinguish changes due to AD and due to other degenerative conditions. According to Growdon et al. (Neurobiol. Aging, 1998, 19:109-116), the ideal marker for AD should meet the following requirements:

It should detect a fundamental feature of the neuropathology

It should be validated in neuropathologically-confirmed cases of the disease

It should show a sensitivity of at least 80% for detecting AD

It should show a specificity of at least 80% to distinguish AD from other types of dementia and It should be reliable, reproducible, non-invasive, simple to perform and inexpensive.

SUMMARY OF THE INVENTION

In one aspect, the invention relates to an antibody which specifically binds to the Aβ(1-17) peptide.

In a second aspect, the invention relates to a kit for the detection of the Aβ(1-17) peptide, comprising:
(i) a first antibody which is an antibody as defined in any of claims 1 to 3 and
(ii) a second antibody which recognises a region of the Aβ(1-17) peptide different from the region that is recognised by the first antibody.

In a third aspect, the invention relates to a method for determining or detecting the Aβ(1-17) peptide in a sample comprising the steps of:
(i) capturing the Aβ(1-17) peptide present in the sample with a first antibody which binds specifically to said peptide,
(ii) contacting the immune complexes formed in step (i) with a second antibody, wherein said second antibody is as defined in any of claims 1 to 4 and wherein said second antibody recognises a different region than the first antibody and is coupled to a first member of a binding pair;
(iii) contacting the complexes formed in step (ii) with a second member of a binding pair which is coupled to a detectable tag, and (iv) detecting or determining the activity or amount of the detectable tag.

In another aspect, the invention relates to a method for the monitoring of a neurodegenerative disease in a subject, comprising:
  (a) determining in a sample from said subject at a first time point the level of the free Aβ17 peptide in a plasma sample and the level of Aβ17 peptide bound to cells in a blood sample in a sample of said subject;
  (b) determining in a sample from said subject at a second time point the level of the free Aβ17 peptide in a plasma sample and the level of Aβ17 peptide bound to cells in a blood sample of said subject and
  (c) comparing the ratio of level of free Aβ17 peptide in a plasma sample and the level of Aβ17 peptide bound to cells in a blood sample at said first and second time points;

wherein if said ratio is increased at the second time point with respect to the first time point, it is indicative of a worsening of Alzheimer's disease in the subject between said first and said second time points.

In another aspect, the invention relates to a method for determining whether a subject is suffering from mild Alzheimer's disease comprising determining the value of one or more parameters selected from the group of consisting of:
  (a) the added values of Aβ17, Aβ40 and Aβ42 peptides levels bound to cells in a blood sample from said subject sample;
  (b) the added values of the Aβ17, Aβ40 and Aβ42 total peptides levels in a plasma sample from said subject and the Aβ17, Aβ40 and Aβ42 peptides levels bound to cells in a blood sample from said subject;
  (c) the added value of total Aβ42 peptide level in a plasma sample from the subject and the level of Aβ42 peptide bound to cells in a blood sample from the subject;
  (d) the added values of total Aβ40 and Aβ42 peptides levels in a plasma sample from the subject and the Aβ40 and Aβ42 peptides levels bound to cells in a blood sample from the subject; and
  (e) the ratio value between the level of the free Aβ17 in a plasma sample from said subject and the Aβ17 peptide bound to cells in a blood sample from the subject;

wherein if the value of one or more of said parameters is increased with respect to the value of said parameters in a reference sample of a healthy subject, then the subject is suffering from mild Alzheimer's disease.

In another aspect, the invention relates to a method for determining whether a subject suffers from MCI with prodromal Alzheimer's disease comprising determining the value of one or more parameters selected from the group of:
  (a) the added values of the total Aβ42 peptide level in a plasma sample from said subject and the Aβ42 peptide level bound to cells in a blood sample of said subject;
  (b) the added values of the total Aβ40 and Aβ42 peptides level in a plasma sample from the subject and the Aβ40 and Aβ42 peptides levels bound to cells in a blood sample from said subject;
  (c) the ratio value between the level of the free Aβ17 peptide in a plasma sample from the subject and the level of Aβ17 peptide bound to cells in a blood sample from said subject;
  (d) the ratio value between the level of Aβ17 bound to cells in a blood sample and the level of Aβ42 peptide bound to cells in a blood sample;
  (e) the ratio value between two parameters, wherein the first parameter corresponds to the added levels of total Aβ17 peptide in a plasma sample and the level of Aβ17 peptide bound to cells in a blood sample and the second parameter correspond to the added levels of total Aβ42 peptide in a plasma sample and the level of Aβ42 peptide bound to cells in a blood sample;
  (f) the ratio value between two parameters, wherein the first parameter corresponds to the level of Aβ17 peptide bound to cells in a blood sample and the second parameter corresponds to the added value of the levels of the Aβ40 peptide bound to cells in a blood sample and of the Aβ42 peptide bound to cells in a blood sample; and
  (g) the ratio value between two parameters, wherein the first parameter corresponds to the added values of the level of total Aβ17 peptide in a plasma sample from said subject and the level of the Aβ17 peptide bound to cells in a blood sample and the second parameter corresponds to the added value of the total Aβ40 and Aβ42 peptides in a plasma sample and the levels of Aβ40 and Aβ42 peptides bound to cells in a blood sample;

wherein if the value of one or more of the parameters (a), (b) or (c) is increased and/or the value of one or more of the parameters (d), (e), (f) or (g) is decreased with respect to the value in a reference sample of a healthy subject, the subject is suffering from MCI with prodromal Alzheimer's disease.

In another aspect, the invention relates to a method for determining whether a subject is suffering from MCI with prodromal Alzheimer's disease comprising determining the value of one or more parameters selected from the group of:
  (a) the added values of Aβ17, Aβ40 and Aβ42 peptides levels bound to cells in a blood sample from said subject sample;
  (b) the ratio value between the Aβ17 peptide level bound to cells in a blood sample of the subject and the Aβ42 peptide level bound to cells in a blood sample of said subject;
  (c) the ratio value between two parameters, wherein the first parameter corresponds to the added values of Aβ17 total peptide level in a plasma sample from said subject and the level of Aβ17 peptide bound to cells in a blood sample and the second parameter corresponds to the added values of Aβ42 total peptide level in a plasma sample from said subject and the level of Aβ42 peptide bound to cells in a blood sample;
  (d) the ratio value between two parameters, wherein the first parameter corresponds to the level of Aβ17 peptide bound to cells in a blood sample and the second parameter corresponds to the added values of the Aβ40 and Aβ42 peptides levels bound to cells in a blood sample;
  (e) the ratio value between two parameters, wherein the first parameter corresponds to the added values of the Aβ17 total peptide level in a plasma sample from said subject and the Aβ17 peptide level bound to cells in a blood sample and the second parameter corresponds to the added values of Aβ40 and Aβ42 total peptides levels in a plasma sample and of Aβ40 and Aβ42 peptide levels bound to cells in a blood sample;

wherein if the value of (a) is increased and/or the value of one or more of said parameters (b), (c), (d) and (e) is decreased with respect to the value of a reference sample of a subject suffering from MCI with non-prodromal Alzheimer's disease, the subject is suffering from MCI with prodromal Alzheimer's disease.

In another aspect, the invention relates to a method for determining whether a subject is suffering from mild Alzheimer's disease comprising determining the value of one or more parameters selected from the group of:
  (a) the added values of the Aβ17, Aβ40 and Aβ42 peptides levels bound to cells in a blood sample;

(b) the added values of the Aβ17, Aβ40 and Aβ42 total peptides levels in a plasma sample and the levels of the Aβ17, Aβ40 and Aβ42 peptides bound to cells in a blood sample;

(c) the added values of total Aβ42 peptide in a plasma sample and the level of Aβ42 peptide bound to cells in a blood sample;

(d) the added values of the total Aβ40 and Aβ42 peptides levels in a plasma sample and the levels of the Aβ40 and Aβ42 peptides bound to cells in a blood sample;

(e) the added values of total Aβ40 peptide level in a plasma sample and the level of Aβ40 peptide bound to cells in a blood sample;

(f) the ratio value between two parameters, wherein the first parameter corresponds to the level of the Aβ17 peptide bound to cells in a blood sample and the second parameter corresponds to the added values of the levels of Aβ40 and Aβ42 peptides bound to cells in a blood sample; and (g) the ratio value between the level of the free Aβ17 peptide in a plasma sample and the Aβ17 peptide level bound to cells in a blood sample;

wherein if the value of one or more of said parameters is increased with respect to the value of a reference sample of a subject having MCI with non-prodromal Alzheimer's disease, the subject is suffering from mild Alzheimer's disease.

In another aspect, the invention relates to a method for determining whether a subject is suffering from mild Alzheimer's disease comprising determining the value of one or more parameters selected from the group of:

(a) the ratio value between the free Aβ17 peptide level in a plasma sample and the level of the Aβ40 peptide free in a plasma sample; and (b) the ratio between two parameters, wherein the first parameter corresponds to the level of the free Aβ17 peptide in a plasma sample and the second parameter corresponds to the added levels of the Aβ40 and Aβ42 peptides free in a plasma sample;

wherein if the value of one or more of said parameters is increased with respect to the value of a reference sample of a prodromal mild cognitive impairment subject, the subject is suffering from mild Alzheimer's disease.

DETAILED DESCRIPTION OF THE INVENTION

Figure 1:
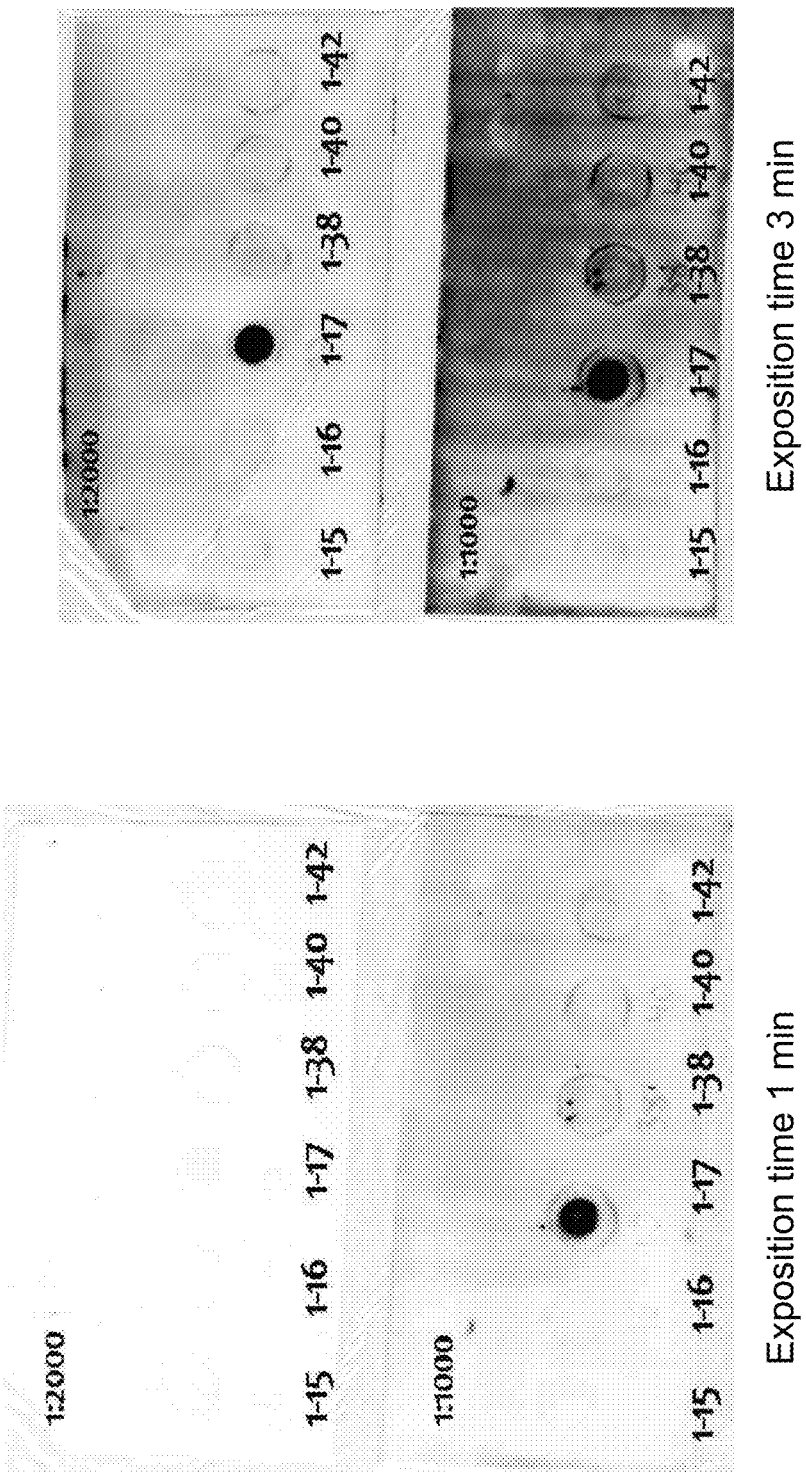
FIG. 1: Result of a dot blot assay carried out using the polyclonal anti-Aβ(1-17) antibody and different Aβ peptides adsorbed to a membrane. The secondary antibody used in the assay was a goat anti-rabbit antibody-HRP. The dot-blot was developed with ECL with the SNAP technology at 1 minute and 3 minutes exposition.

The authors of the present invention have generated an antibody highly specific for the Aβ17 peptide, which does not recognize other Aβ species. For instance, FIG. 1 shows that the antibody recognises Aβ17 in a specific manner without showing any substantial cross-reactivity towards other Aβ species such as Aβ15, Aβ16, Aβ38, Aβ40 or Aβ42. They have also designed a kit for the detection of the Aβ17 peptide allowing a reliable quantification of said molecular species in any sample in any subject and, in particular, in the plasma from subjects suspected of suffering AD. Likewise, the authors have shown that it is possible to distinguish between different groups of subjects: healthy, prodromal AD, non-prodromal mild cognitive impairment and mild AD subjects by measuring the level of different parameters.

Antibody of the Invention

In a first aspect, the invention relates to an antibody, hereinafter the antibody of the invention, which specifically binds to the Aβ(1-17) peptide (SEQ ID NO:1).

The term "specifically binds", as used herein, refers to an antibody which binds to the Aβ17 peptide without giving any substantial cross-reaction with other Aβ peptides. In a particular embodiment, the specificity for the Aβ17 peptide is higher than 50%, higher than 60%, higher than 70%, higher than 80% or higher than 90%. More preferably, the specificity of the antibody for the Aβ17 peptide is higher than 95%. As can be seen in FIG. 1, the authors of the invention have assayed the specificity of the anti-Aβ17 antibody and they have showed that it is highly specific for the Aβ17 peptide and it does not show substantial cross-reactivity to other Aβ peptides (Aβ15, Aβ16, Aβ38, Aβ40 and Aβ42). Thus, in a particular embodiment the antibody of the invention does not show substantial cross-reactivity towards a Aβ peptide selected from the group consisting of Aβ15, Aβ16, Aβ38, Aβ40, Aβ42 and a combination of one or more of them There is practically no limitation with regard to the type of antibody according to the present invention, as long as it contains at least one antigen binding site specific for Aβ17. Therefore, antibodies molecules suitable include:

"intact" antibodies which comprise an antigen-binding variable region as well as a light chain constant domain (CL) and heavy chain constant domains, CH1, CH2 and CH3, "Fab" fragments resulting from the papain digestion of an intact antibody and which comprise a single antigen-binding site and a CL and a CH1 region, "F(ab')₂" fragments resulting from pepsin digestion of an intact antibody and which contain two antigen-binding sites, "Fab'" fragments containing the constant domain of the light chain and the first constant domain (CH1) of the heavy chain and which have one antigen-binding site only. Fab' fragments differ from Fab fragments by the addition of a few residues at the carboxy terminus of the heavy chain CH 1 domain including one or more cysteines from the antibody hinge region.

"Fv" is the minimum antibody fragment which contains a complete antigen-recognition and antigen-binding site. This region consists of a dimer of one heavy chain and one light chain variable domain in tight, non-covalent-association. It is in this configuration that the three hypervariable regions (CDRs) of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

Single-chain FV or "scFv" antibody fragments comprise the VL and VH, domains of antibody, wherein these domains are present in a single polypeptide chain. Preferably, the VL and VH regions are connected by a polypeptide linker which enables the scFv to form the desired structure for antigen binding.

"Diabodies" comprise a heavy chain variable domain (VH) connected to a light chain variable domain (VL) on the same polypeptide chain (VH-VL) connected by a peptide linker that is too short to allow pairing between the two domains on the same chain. This forces pairing with the complementary domains of another chain and promotes the assembly of a dimeric molecule with two functional antigen binding sites.

"Bispecific antibodies" (BAbs) are single, divalent antibodies (or immunotherapeutically effective fragments thereof) which have two differently specific antigen binding sites. The two antigen sites may be coupled together chemically or by genetic engineering methods known in the art.

All these antibody fragments can be further modified using conventional techniques known in the art, for example, by using amino acid deletion(s), insertion(s), substitution(s), addition(s), and/or recombination (and/or any other modification(s) (e.g. posttranslational and chemical modifications, such as glycosylation and phosphorylation) known in the art), either alone or in combination. Methods for introducing such modifications in the DNA sequence underlying the amino acid sequence of an immunoglobulin chain are well known to the person skilled in the art; see, e.g., Sambrook et al.; Molecular Cloning: A Laboratory Manual; Cold Spring Harbor Laboratory Press, $2^{nd}$ edition 1989 and 3rd edition 2001.

Antibodies suitable for the present invention include both polyclonal and monoclonal antibodies. For the production of polyclonal antibodies, various hosts including goats, rabbits, rats, mice, sheep, dogs, camels, dromedaries, llamas, humans, birds and others may be immunized by injection with the peptide corresponding to the fragment of Aβ17 which has immunogenic properties. Depending on the host species, various adjuvants may be used to increase immunological response. Such adjuvants include, but are not limited to, Freund's, mineral gels such as aluminium hydroxide, and surface active substances such as lysolecithin, polyanions, peptides, oil emulsions, KLH, and dinitrophenol. Among adjuvants used in humans, BCG (Bacille Calmette-Guerin) and *Corynebacterium parvum* are especially preferable. In a preferred embodiment, the adjuvants used for the generation of the antibody of the invention are Freund's Complete Adjuvant, Freund's Incomplete Adjuvant and Imject Alum.

It may be useful to conjugate the antigen to a protein that is immunogenic in the species to be immunized. Proteins useful for conjugation with the peptide are, without limitation, keyhole limpet hemocyanin (KLH), Blue Carrier (hemocyanin isolated from *Concholepas concholepas*), bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride or $SOCl_2$. In a preferred embodiment, the protein used for conjugation is KLH. In a preferred embodiment, the conjugation between the peptide and KLH is carried out through the crosslinker NHS-$PEG_4$-Maleimide and the peptides have a cysteine in N-terminal to perform the conjugation of the peptide to the KLH.

For the production of monoclonal antibodies, conventional techniques can be used. For instance, monoclonal antibodies may be made using the hybridoma method first described by Kohler et al., Nature, 256:495 (1975) using the procedure described in detail in units 11.4 to 11.11 of Ausubel, F. M. et al. (Current Protocols in Molecular Biology, John Wiley & Sons Inc; ring-bound edition, 2003). Alternatively, monoclonal antibodies can be isolated by recombinant DNA procedures from antibody phage libraries generated using the techniques described in McCafferty et al., Nature, 348:552-554 (1990). Clacksoii et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nucl. Acids. Res., 21:2265-2266 (1993)). Thus, these techniques are viable alternatives to traditional monoclonal antibody hybridoma techniques for isolation of monoclonal antibodies.

Polyclonal antibodies can be used directly as an antiserum obtained from immunised hosts after bleeding and removal of the fibrin clot. Monoclonal antibodies can be used directly as the supernatant of the hybridoma culture or as ascites fluid after implantation of the hybridoma in the peritoneal cavity of a suitable host. Alternatively, the immunoglobulin molecules, either polyclonal or monoclonal, can be purified prior to their use by conventional means such as affinity purification using peptides derived from Aβ17, non-denaturing gel purification, HPLC or RP-HPLC, size exclusion, purification on protein A column, or any combination of these techniques.

In a preferred embodiment the antibody of the invention is a policlonal antibody. In a preferred embodiment, the method for the generation of the antibody of the invention includes the following steps:
- 1$^{st}$ dose: Immunization of a rabbit with 100 μg of the peptide using Freund's Adjuvant Complete as adjuvant.
- 2$^{nd}$ dose: Immunization of a rabbit with 100 μg of the peptide using Freund's Adjuvant Incomplete as adjuvant.
- 3$^{rd}$ dose: Immunization of a rabbit with 100 μg of the peptide using Alum as adjuvant.
- 3 more doses with 200 μg of the peptide alternating the adjuvants: Freund's Adjuvant Incomplete-Alum-Freund's Adjuvant Incomplete.

In a preferred embodiment the region of the Aβ peptide or immunogen used for generating the antibody of the invention is selected from the group consisting of peptide Aβ(12-17), corresponding to the sequence VHHQKL (SEQ ID NO:2) and from the peptide Aβ(11-17), corresponding to the sequence EVHHQKL (SEQ ID NO:3).

Kit of the Invention

In a second aspect, the invention relates to a kit for the detection or for the determination of the Aβ(1-17) peptide, hereinafter kit of the invention, comprising:
- (i) a first antibody which is the antibody specific for Aβ(1-17) according to the invention and
- (ii) a second antibody which recognises a region of the Aβ(1-17) peptide different from the region that is recognised by the first antibody.

The term "amyloid beta peptide" is used herein interchangeably with Aβ, amyloid beta protein, "A beta," "beta AP," or "A beta peptide" refers to a family of peptides that are the principal chemical constituent of the senile plaques and vascular amyloid deposits (amyloid angiopathy) found in the brain in patients of Alzheimer's disease (AD), Down's Syndrome, and Hereditary Cerebral Hemorrhage with Amyloidosis of the Dutch-Type (HCHWA-D). In whatever form, amyloid beta peptide is a fragment of beta-amyloid precursor protein (APP) which comprises a variable number of amino acids which is produced by the sequential proteolytic cleavage of the amyloid precursor protein by the β- and γ-secretases or by β- and α-secretases.

Amyloid beta peptides are commonly expressed as "Aβ(x-y)" wherein x represents the amino acid number of the amino terminus of the amyloid beta peptides and y represents the amino acid number of the carboxy terminus. "Aβ(1-17)" or "Aβ17", as used herein, relates to a 17 amino acids peptide corresponding to amino acids 672 to 688 (SEQ ID NO:1) of the amyloid precursor protein and which is produced by the sequential proteolytic cleavage of the amyloid precursor protein (SEQ ID NO:4) by the β- and α-secretases.

In the context of the present invention, the "capture antibody" is the antibody which is used to retrieve from a sample all molecular species to which the antibody specifically binds. There is practically no limitation with regard to the type of antibody that can be used as capture antibody as long as it contains at least one antigen binding site specific for Aβ17. In principle, any antibody specific for the Aβ17 peptide can be used as capture antibody. The capture antibody binds to a different region than the second antibody. In a preferred embodiment, the capture antibody is directed against an epitope of the N-terminal region of the Aβ17 peptide. In a still more preferred embodiment, epitopes which can be targeted by the capture antibody include epitopes located within amino acids 1 to 10 of Aβ17. In yet another preferred embodiment, the capture antibody is a monoclonal antibody. In a still more preferred embodiment, the capture antibody recognises a region corresponding to amino acids 1-16 of the Aβ peptide. In a still more preferred embodiment, the monoclonal antibody used as capture antibody is the 6E10 mAb as has been described in Kim, K. S. (Neuroscience Res. Comm. 1988, 2:121-130).

The second component of the kit of the invention corresponds to the antibody of the invention, already described previously in the present invention. In the context of the present invention, the "detection antibody" is the antibody which will be used to detect the amount of antigen which has been retained by the capture antibody. The first antibody recognizes a different region than the second antibody, because it must bind to a region of the antigen which is not covered by the capture antibody.

The first and the second antibody can be used in the kit of the invention indistinctly as capture and detection antibodies.

One of the two antibodies (the first or the second antibody) may be coupled to a first member of a binding pair, so as to allow the detection of the antibody which is bound to the antigen captured by the capture antibody. The antibody which will be coupled will act as detection antibody and may be either the first or the second antibody.

In a particular embodiment, the kit further comprises an antibody or combination of antibodies which specifically bind to Aβ40 and/or Aβ42. Thus, in a particular embodiment, the kit would be useful for the detection of the Aβ17 peptide and the Aβ40 and/or Aβ42 peptide/s.

"Aβ42", as used herein, relates to a 42 amino acids peptide corresponding to amino acids 672 to 713 (SEQ ID NO:5) and which is produced by the sequential proteolytic cleavage of the amyloid precursor protein (SEQ ID NO:4) by the β- and γ-secretases. "Aβ40", as used herein, relates to a 40 amino acids peptide corresponding to amino acids 672 to 711 (SEQ ID NO:6) and which is produced by the sequential proteolytic cleavage of the amyloid precursor protein (SEQ ID NO:4) by the β- and γ-secretases.

In a preferred embodiment, the first or second antibody, as the case may be, is coupled to a first member of a binding pair. If this is the case, a second member of a binding pair coupled to a detectable tag is also included in the kit. In a particular embodiment, if the detectable tag which is coupled to the second member of the binding pair is an enzyme tag, then the kit further comprises a substrate which can be converted by said enzyme into a detectable product.

Suitable first and second members of binding pairs include, without limitation:
- hapten or antigen/antibody, e.g. digoxin and anti-digoxin antibodies,
- biotin or biotin analogues (e.g. aminobiotin, iminobiotin or desthiobiotin)/avidin or streptavidin,
- sugar/lectin,
- enzyme and cofactor,
- folic acid/folate,
- double stranded oligonucleotides that selectively bind to proteins/transcription factors,
- nucleic acid or nucleic acid analogue/complementary nucleic acid, and
- receptor/ligand, e.g., steroid hormone receptor/steroid hormone.

It will be understood that the term "first" and "second" member of a binding pair is relative and that each of the above members can be seen as first or second members of the binding pair. In a preferred embodiment, the first member of a binding pair is biotin or a functionally equivalent variant thereof and the second member of the binding pair is avidin, streptavidin or a functionally equivalent variant thereof. In a preferred embodiment, the second member of the binding pair is streptavidin.

Suitable detectable tags include, without limitation, fluorescent moieties (e.g., fluorescein, rhodamine, phycoerythrin, coumarin, oxazine, resorufin, cyanine and derivatives thereof), luminescent moieties (e.g., Qdot™ nanoparticles supplied by the Quantum Dot Corporation, Palo Alto, Calif.). If the detectable tag is an enzyme, then this enzyme must be capable of generating a detectable signal, for example, upon addition of an activator, substrate, amplifying agent and the like. Enzymes which are suitable as detectable tags for the present invention and its corresponding substrates include:

Alkaline phosphatase:
  Chromogenic substrates: Substrats based on p-nitrophenyl phosphate (p-NPP), 5-bromo-4-chloro-3-indolyl phosphate/nitroblue tetrazolium (BCIP/NBT), Fast-Red/naphthol-AS-TS phosphate
  Fluorogenic substrates: 4-methylumbelliferyl phosphate (4-MUP), 2-(5'-chloro-2'-phosphoryloxyphenyl)-6-chloro-4-(3H)-quinazolinone (CPPCQ), 3,6-fluorescein diphosphate (3,6-FDP), Fast Blue BB, Fast Red TR, or Fast Red Violet LB diazonium salts
Peroxidases:
  Chromogenic substrates based on 2,2-azinobis(3-ethylbenzothiazoline-6-sulfonic acid) (ABTS), o-phenylenediamine (OPT), 3,3',5,5'-tetramethylbenzidine (TMB), o-dianisidine, 5-aminosalicylic acid, 3-dimethylaminobenzoic acid (DMAB) and 3-methyl-2-benzothiazolinehydrazone (MBTH), 3-amino-9-ethylcarbazole (AEC)— and 3,3'-diaminobenzidine tetrahydrochloride (DAB).
  Fluorogenic susbtrates: 4-hydroxy-3-methoxyphenylacetic acid, reduced phenoxazines and reduced benzothiazines, including Amplex® Red reagent, Amplex UltraRed and reduced dihydroxanthenes.
Glycosidases:
  Chromogenic substrates: o-nitrophenyl-β-D-galactoside (o-NPG), p-nitrophenyl-β-D-galactoside and 4-methylumbelliphenyl-β-D-galactoside (MUG) for β-D-galactosidase.
  Fluorogenic substrates: resorufin β-D-galactopyranoside, fluorescein digalactoside (FDG), fluorescein diglucuronide, 4-methylumbelliferyl β-D-galactopyranoside, carboxyumbelliferyl β-D-galactopyranoside and fluorinated coumarin β-D-galactopyranosides.
Oxidoreductases (luciferase):
  Luminescent substrates: luciferin.

In a particular embodiment, the detectable tag is a fluorescent molecule, a luminescent molecule or an enzyme. In a preferred embodiment, the detectable tag is horseradish peroxidase and the detection reagent is TMB.

In a preferred embodiment, the kit further comprises a solid support. As used herein, the term "support" or "surface" refers to a solid phase which is a porous or non-porous water insoluble material that can have any one of a number of shapes, such as strip, rod, particles, including latex particles, magnetic particles, microparticles, beads, membranes, microtiter wells and plastic tubes. In principle, any material is suitable as solid support provided that is able to bind sufficient amounts of the capturing antibody. Thus, the choice of solid phase material is determined based upon desired assay format performance characteristics. Materials suitable for the solid support include polymeric materials, particularly cellulosic materials and materials derived from cellulose, such as fibre containing papers, e.g., filter paper, chromatographic paper, glass fiber paper, etc.; synthetic or modified naturally occurring polymers, such as nitrocellulose, cellulose acetate, poly (vinyl chloride), polyacrylamide, cross linked dextrane, agarose, polyacrylate, polyethylene, polypropylene, poly(4-methylbutene), polystyrene, polymethacrylate, poly(ethylene terephthalate), nylon, polyvinyl butyrate), etc.; either used by themselves or in conjunction with other materials; glass such as, e.g., glass available as bioglass, ceramics, metals, and the like. Non-crosslinked polymers of styrene and carboxylated styrene or styrene functionalized with other active groups such as amino, hydroxyl, halo and the like are preferred. In some instances, copolymers of substituted styrenes with dienes such as butadiene will be used.

In a particular embodiment, the antibody which is not coupled to a first member of a binding pair is prebound to the solid support, which can be the first or the second antibody. The solid support and the first or second antibody may be separately provided in the kit or, alternatively, the support may be delivered already precoated with the antibody. In this case, the support may have been treated with a blocking solution after the binding of the antibody. If the support is precoated, it is preferred that the support is treated with a concentrated trehalose solution and allowed to dry, in which case the dry trehalose forms a halo on the support. These supports containing the dry trehalose are exceptionably stable and can be stored for up to two years when kept at 4° C. in the dark.

Additional components of the kit may include:
  Means for recovering from the patient the sample to be analysed.
  Buffers and solutions required for preparing the standard curves of the target peptides.
  Buffers and solutions for washing and blocking the solid support during the assay
  Buffers and solutions for coating the solid support with the coating antibody
  Reagents for developing the coloured or fluorogenic signal from the detectable tag.
  Reagents for stopping the formation of the coloured or fluorogenic product from the detectable tag (e.g. 1N $H_2SO_4$)
  Means for maintaining the peptides in an unfolded state (e.g. concentrated guanidinium hydrochloride).
  A sample containing a stock solution of the Aβ17 peptide and additionally of Aβ40 and/or Aβ42 peptides or a combination thereof.

The immobilisation of the antibody into the solid support can be carried out prior to the binding of the target peptide to be detected or once the peptide/protein is bound to the antibody. In any, case, if a solid support is used, it is convenient to block the excess of protein binding sites on the carrier prior to the addition of the sample containing the target peptide to be determined. Preferably, blocking or quenching of the peptide-binding sites on the support is carried out using the same buffer which is used for washing the complexes after each binding reaction (e.g. 50 mM Tris-HCl, pH 8, PBS or TBS optionally, comprising Tween 20) supplemented with a macromolecular compound (e.g. bovine serum albumin, non-fat dry milk, western blocking reagent, caseine, lactoalbumine, ovoalbumine) in concentrations from about 0.05% to 10%, preferably 1 to 5%, more preferably around 3%. If the support comprising the immobilised capture antibody must be stored for some time, it is preferred that the support is treated with a concentrated trehalose solution and allowed to dry, in which case the dry trehalose forms a halo on the support. These supports containing the dry trehalose are exceptionably stable and can be stored up to two years when kept at 4° C. in the dark.

The kit of the invention allows the detection or determination with high sensitivity and specificity of the peptide or peptides which are specifically recognised by the first and second antibody components of the kit. Thus, in a further aspect, the invention relates to the use of a kit of the invention to detect the Aβ17 peptide in a sample. In a particular embodiment, the kit is used to detect optionally the Aβ40 and/or Aβ42 peptides and the combination thereof in a sample.

In view of the ability of the kit of the invention to provide high sensitivity and specificity determination of the concentration of the Aβ17 peptide in any sample, it can be used for the diagnosis of any disease wherein there is an altered concentration of any of this peptide in any cell fluid or tissue, in particular, degenerative diseases and, more particularly, neurodegenerative diseases. Non limitative examples of degenerative diseases which may be diagnosed based on the appearance of altered levels of Aβ17 or of altered levels of Aβ40 or Aβ42 include:

bone degenerative disorders such as osteopenia, osteomalacia, osteoporosis, osteomyeloma, osteodystrophy, Paget's disease, osteogenesis imperfecta, bone sclerosis, aplastic bone disorder, humoral hypercalcemic myeloma, multiple myeloma and bone thinning following metastasis.

cartilage degenerative disorders such as Gorham-Stout syndrome; arthritic diseases; osteoarthritis; rheumatoid arthritis; psoriatic arthritis; rheumatoid disease; and brittle bone disease.

muscle degenerative diseases such as muscular dystrophy, muscle atrophy, congestive obstructive pulmonary disease, muscle wasting syndrome, sarcopenia, cachexia.

heart degenerative diseases including cardiac cell death due to ischemia, tissue and organ death due to transplant rejection, hearing loss due to autotoxicity.

retinal degenerative disorders such as retinitis pigmentosa degenerative diseases of the nervous system such as Alexander disease, Alper's disease, Alzheimer's disease, Amyotrophic lateral sclerosis, Ataxia telangiectasia, Bovine spongiform encephalopathy (BSE), Canavan disease, Cockayne syndrome, Corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), Multiple sclerosis, Multiple System Atrophy, Neuroborreliosis, Parkinson disease, Pelizaeus-Merzbacher Disease, Pick's disease, Primary lateral sclerosis, Prion diseases, Refsum's disease, Sandhoff disease, Schilder's disease, Schizophrenia, Spielmeyer-Vogt-Sjogren-Batten disease (also known as Batten disease), Spinocerebellar ataxia, spinal muscular atrophy, Steele-Richardson-Olszewski disease, Tabes dorsalis. In a preferred embodiment, the neurodegenerative disorder that is diagnosed using the kit of the invention is Alzheimer's disease.

Method for Determining or Detecting the Aβ17 Peptide

The kit of the invention allows to carry out a method for determining or detecting the Aβ17 peptide in a sample. Thus, in another aspect, the invention relates to a method for determining or detecting the Aβ(1-17) peptide in a sample, hereinafter the method for detection of the invention, comprising the steps of:

(i) capturing the Aβ(1-17) peptide present in the sample with a first antibody which binds specifically to said peptide, (ii) contacting the immune complexes formed in step (i) with a second antibody, wherein said second antibody is as defined in any of claims 1 to 4 and wherein said second antibody recognises a different region than the first antibody and is coupled to a first member of a binding pair;

(iii) contacting the complexes formed in step (ii) with a second member of a binding pair which is coupled to a detectable tag, and (iv) detecting or determining the activity or amount of the detectable tag.

A "sample", as understood in the present invention, includes any one of tissue culture, plasma, serum, saliva, semen, sputum, cerebral spinal fluid (CSF), tears, mucus, sweat, milk, brain or peripheral tissue extracts and the like. In a preferred embodiment, the sample is selected from the group of blood, serum, plasma and CSF. In a more preferred embodiment, the sample is a plasma sample.

In a preferred embodiment, the peptides which are detected correspond to non-oligomeric forms of said peptide, more preferably, monomeric forms of Aβ17.

The reagents and the antibodies used in each steps of the method have been described in detail above for the kit of the invention.

In the first step of the method according to the present invention, the sample which contains Aβ17 peptides is contacted with a first antibody so as to form a first immune complex. In a preferred embodiment, the first antibody is a monoclonal antibody. In a more preferred embodiment the monoclonal antibody is the 6E10 antibody.

After the first binding step has been carried out, the complexes can be washed to remove any excess of protein/peptide found in the original sample which did not bind to the capture antibody. Preferred washing buffers that can be used in the context of the present invention include any buffer at a pH close to physiological (e.g. 50 mM Tris-HCl) optionally comprising salts (e.g. 150 mM NaCl) and optionally comprising low concentrations of a detergent (e.g. 0.05% Tween-20).

In a second step, the complexes formed between the capture antibody and the Aβ peptide in the sample are then contacted with the second antibody so as to form a "sandwich-type" immune complex. The first antibody and the second antibody will bind to a different region of the Aβ17 peptide, so there is no interference between them.

The first and second step of the present method can be interchanged and the capture of the Aβ17 peptide can be performed by the second antibody (the antibody of the invention). The complex is then contacted with the first antibody, which will bind in a different region as the second antibody. One of the two antibodies will be coupled to a first member of a binding pair, which will correspond to the antibody which is not used in the capture step.

After the second step is carried out, the immune complex can be washed to eliminate unspecifically-bound antibodies using essentially the same buffers and procedures as described before.

In a third step, the method of the invention involves contacting the complexes formed between the capture antibody-antigen and the detection antibody coupled with a first member of a binding pair with a second member of a binding pair which is coupled to a detectable tag. In a preferred embodiment, the first member of a binding pair is biotin and the second member of a binding pair is avidin, streptavidin or a functionally equivalent variant thereof.

In the fourth step of the method according to the invention, the method involves detecting the detectable tag. It will be understood that the detection and/or the quantification of the detectable tag depend on the nature of the tag and are techniques known in the art. When an intact substrate or detectable tag contains a luminescent or dye component, detection can be by visual observation on a UV transiluminator, or by using a UV-based charged coupled device (CCD) camera detection system, a laser-based gel scanner, a xenon-arc-based CCD camera detection system, a Polaroid camera combined with a UV-transiluminator, as well as a variety of other devices used for detecting luminescence. When the detectable tag is an enzyme, the fourth step of the method according to the invention involves exposing the immunocomplexes labelled with the tag (e.g., the captured peptide, the detection antibody and the reagent labelled with the detectable tag) to activators, substrates, or amplifying agents of the enzyme used as detectable tag. Well known detectable tags capable of generating a detectable signal include enzyme-labeled antibodies. Exemplary enzymes well known for this purpose include horseradish peroxidase, alkaline phosphatase and glycosidases, including β-galactosidase, β-glucosidase and β-glucuronidase. As an example, a reagent which specifically binds to the detection antibody can be tagged with horseradish peroxidase. Upon formation of a capture moiety-detection antibody-reagent complex, detection can then be performed using any of a wide range of well known substrates for the enzyme used as detectable tags. In a preferred embodiment, the detectable tag is a fluorescent molecule, a luminescent molecule or an enzyme.

In a particular embodiment, the method for detection of the invention further comprises the detection of Aβ40 and/or Aβ42 peptides.

Method for Monitoring the Progression of a Neurodegenerative Disease

In another aspect, the invention relates to a method for the monitoring of a neurodegenerative disease in a subject, hereinafter method for monitoring of the invention, comprising determining in a sample at a first time point the level of the Aβ17 peptide free in plasma and the level of Aβ17 peptide bound to cells in a sample of said subject and comparing the levels with said levels at a second time point; wherein if the ratio of Aβ17 peptide free in plasma and Aβ17 peptide bound to cells is increased at the second time point with respect to the first time point, it is indicative of a worsening of Alzheimer's disease in the subject.

The term "neurodegenerative disease", as used herein, refers to a condition or disorder in which neuronal cells are lost due to cell death bringing about a deterioration of cognitive functions or result in damage, dysfunction, or complications that may be characterized by neurological, neurodegenerative, physiological, psychological, or behavioral aberrations. Suitable neurodegenerative diseases that can be diagnosed with the methods of the invention include, without limitation, age-related macular degeneration, Creutzfeldt-Jakob disease, Alzheimer's Disease, cerebral angiopathy with amyloidosis, vascular dementia, radiotherapy induced dementia, axon injury, acute cortical spreading depression, alpha-synucleinopathies, brain ischemia, Huntington's disease, permanent focal cerebral ischemia, peripheral nerve regeneration, post-status epilepticus model, spinal cord injury, sporadic amyotrophic lateral sclerosis and transmissible spongiform encephalopathy.

In a preferred embodiment, the neurodegenerative disease which is monitored according to the method of the invention is Alzheimer's disease or prodromal forms thereof including mild cognitive impairment, mild cognitive impairment with probable Alzheimer's disease or mild cognitive impairment with possible Alzheimer's disease.

The method for monitoring of the invention is useful for the evaluation of the progression of Alzheimer's disease in a subject. Thus, the authors of the invention have shown that an increase in the ratio of the level of Aβ17 peptide free in plasma/level of Aβ17 peptide bound to cells is indicative of a worsening of AD.

In a particular embodiment, the method for monitoring of the invention comprises the following steps:
(a) determining the concentration of the Aβ17 peptide free in plasma and the level of Aβ17 peptide bound to cells in a sample of a subject, at a first time point; (FP Aβ17/CB Aβ17),
(b) determining the concentration of the Aβ17 peptide free in plasma and the level of Aβ17 peptide bound to cells in a sample of the same subject, at a second time point;
The time points chosen are to be determined by the skilled person, according to the subject.
(c) comparing the ratio of the level of Aβ17 peptide free in plasma/level of Aβ17 peptide bound to cells between the first time point and the second time point and
(d) if the ratio of said parameters is higher in the second time point with respect to the first time point, it is indicative of a worsening of Alzheimer's disease in the subject.

The term "worsening of Alzheimer's disease", as used herein, means that the disease is progressing to a later stage with respect to stage at the first time point measured. A skilled person will recognize and confirm if the progression of the disease is worsening by analysing also other indicative features. The features or indications which appear in a later stage, and which are indicative of a progression of the disease, are, without limiting, the appearance of amyloid plaques and neurofibrillary tangles and a faster decline in cognitive functions. In a preferred embodiment, if the ratio of the level of Aβ17 peptide free in plasma/level of Aβ17 peptide bound to cells is increased at the second time point with respect to the first time point, it is indicative of higher rates of cognitive impairment of the subject. The higher level of Aβ17 peptide found free in plasma is thus indicative of a higher cognitive impairment.

Any method suitable for the determination of peptides can be used in the present invention. By way of example, the concentration of amyloid beta peptide can be determined using one or more techniques chosen from Western blot, immunoprecipitation, enzyme-linked immunosorbent assay (ELISA), surface plasmon resonance, precipitin reaction, a gel diffusion immunodiffusion assay, radioimmunoassay (RIA), fluorescent activated cell sorting (FACS), two-dimensional gel electrophoresis, capillary electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), thin-layer chromatography, protein chip expression analysis and laser densiometry. In a particular embodiment, the determination of the level of said parameters is determined by ELISA. In a preferred embodiment, one of the antibodies used in the ELISA is the antibody of the invention, directed to the C-terminal region of the Aβ17 peptide.

The term "Aβ17 peptide free in plasma" (hereinafter known as FP Aβ17), as used herein, refer to the level of amyloid beta peptides which are not associated to any component of the biological sample and which is readily available for binding to a specific antibody. This peptide may be determined by conventional immunological techniques by contacting the biological sample with an antibody specific for said peptide. In a preferred embodiment, the level of free amyloid peptide is determined in plasma.

The term "Aβ17 peptide level bound to cells" (hereinafter known as CB Aβ17), as used herein, refers to amyloid beta peptides which are non-covalently associated to the surface of the cells present in the biological sample and which is unavailable for binding to antibodies added to the sample and hence, immunologically detectable. Typically, if the biological sample is blood, the amyloid beta peptide is associated to red blood cells, white blood cells, including neutrophils, eosinophils, basophils, lymphocytes and monocytes, and platelets. The amount of amyloid beta peptide associated to cells in a given sample can be determined and this value can be used alone or in combination with other parameters related to amyloid beta peptides in the methods of the invention. For this purpose, it is first required to isolate the cellular fraction from the biological sample. This can be carried out using any technique known to the skilled person such as centrifugation, sedimentation, filtration and the like. Once the cell fraction of a biological sample has been isolated, the cells are contacted with a protein solubilising agent.

The amount of amyloid beta peptide associated to cells in a given sample can be determined and this value can be used alone or in combination with other parameters related to amyloid beta peptides in the methods of the invention. For this purpose, it is first required to isolate the cellular fraction from the biological sample. This can be carried out using any technique known to the skilled person such as centrifugation, sedimentation, filtration and the like. Once the cell fraction of a biological sample has been isolated, the cells are contacted with a protein solubilising agent.

In a preferred embodiment, the sample of the subject is selected from the group of blood, serum, plasma and CSF. In a more preferred embodiment, the sample is a plasma sample.

Methods for Determining Whether a Subject is Suffering from Alzheimer's Disease or from Early Stages of Alzheimer's Disease The authors of the present invention have identified that the levels of certain populations of amyloid beta peptides, either determined directly or by applying certain calculations among them, can be used for determining whether a patient suffers mild Alzheimer's disease, for determining whether a subject suffers prodromal Alzheimer's disease, for distinguishing a subject suffering from non-prodromal mild cognitive impairment from a subject suffering from prodromal Alzheimer's disease, for distinguishing a subject suffering from non-prodromal mild cognitive impairment from a subject suffering from mild Alzheimer's disease or for distinguishing a subject suffering from prodromal Alzheimer's disease from a subject suffering from mild Alzheimer's disease.

Thus, in another aspect, the invention relates to a method for determining whether a subject is suffering from mild Alzheimer's disease comprising determining the value of one or more parameters selected from the group of consisting of:
  (a) the added values of Aβ17, Aβ40 and Aβ42 peptides levels bound to cells in a blood sample from said subject sample;
  (b) the added value of the Aβ17, Aβ40 and Aβ42 total peptides levels in a plasma sample from said subject and the Aβ17, Aβ40 and Aβ42 peptides levels bound to cells in a blood sample from said subject;
  (c) the added value of total Aβ42 peptide level in a plasma sample from the subject and the level of Aβ42 peptide bound to cells in a blood sample from the subject;
  (d) the added values of total Aβ40 and Aβ42 peptides levels in a plasma sample from the subject and the Aβ40 and Aβ42 peptides levels bound to cells in a blood sample from the subject; and
  (e) the ratio value between the level of the Aβ17 free in a plasma sample from said subject and the Aβ17 peptide bound to cells in a blood sample from the subject;
wherein if the value of one or more of said parameters is increased with respect to the value of a reference sample of a healthy subject, then the subject is suffering from mild Alzheimer's disease.

Therefore, the parameters to be measured for the distinction of a healthy subject from a subject suffering from mild Alzheimer's disease are the following:
  (a) CB Aβ17+CB Aβ40+CB Aβ42
  (b) (CB Aβ17+CB Aβ40+CB Aβ42)+(TP Aβ17+TP Aβ40+TP Aβ42)
  (c) TP Aβ42+CB Aβ42
  (d) (TP Aβ40+TP Aβ42)+(CB Aβ40+CB Aβ42)
  (e) FP Aβ17/CB Aβ17

A method for determining whether a subject suffers from MCI with prodromal Alzheimer's disease comprising determining the value of one or more parameters selected from the group of:
  (a) the added values of the total Aβ42 peptide level in a plasma sample from said subject and the Aβ42 peptide level bound to cells in a blood sample of said subject;
  (b) the added values of the total Aβ40 and Aβ42 peptides level in a plasma sample from the subject and the Aβ40 and Aβ42 peptides levels bound to cells in a blood sample from said subject;
  (c) the ratio value between the level of the Aβ17 peptide free in a plasma sample from the subject and the level of Aβ17 peptide bound to cells in a blood sample from said subject;
  (d) the ratio value between the level of Aβ17 bound to cells in a blood sample and the level of Aβ42 peptide bound to cells in a blood sample;
  (e) the ratio value between two parameters, wherein the first parameter corresponds to the added levels of total Aβ17 peptide in a plasma sample and the level of Aβ17 peptide bound to cells in a blood sample and the second parameter correspond to the added levels of total Aβ42 peptide in a plasma sample and the level of Aβ42 peptide bound to cells in a blood sample;
  (f) the ratio value between two parameters, wherein the first parameter corresponds to the level of Aβ17 peptide bound to cells in a blood sample and the second parameter corresponds to the added value of the levels of the Aβ40 peptide bound to cells in a blood sample and of the Aβ42 peptide bound to cells in a blood sample; and
  (g) the ratio value between two parameters, wherein the first parameter corresponds to the added values of the level of total Aβ17 peptide in a plasma sample from said subject and the level of the Aβ17 peptide bound to cells in a blood sample and the second parameter corresponds to the added value of the total Aβ40 and Aβ42 peptides in a plasma sample and the levels of Aβ40 and Aβ42 peptides bound to cells in a blood sample;
wherein if the value of one or more of the parameters (a), (b) or (c) is increased and/or the value of one or more of the parameters (d), (e), (f) or (g) is decreased with respect to the value in a reference sample of a healthy subject, the subject is suffering from mild Alzheimer's disease.

Therefore, the parameters to be measured for the distinction of a healthy subject from a subject suffering from MCI with prodromal Alzheimer's disease are the following:

(a) TP Aβ42+CB Aβ42
(b) (TP Aβ40+TP Aβ42)+(CB Aβ40+CB Aβ42)
(c) FP Aβ17/CB Aβ17
(d) CB Aβ17/CB Aβ42
(e) (TP Aβ17+CB Aβ17)/(TP Aβ42+CB Aβ42)
(f) CB Aβ17/(CB Aβ40+CB Aβ42)
(g) (TP Aβ17+CB Aβ17)/(TP Aβ40+TP Aβ42)+(CB Aβ40+CB Aβ42)

In another aspect, the invention relates to a method for distinguishing a subject suffering from MCI with non-prodromal Alzheimer's disease from a subject suffering from MCI with prodromal Alzheimer's disease comprising determining the value of one or more parameters selected from the group of:
(a) the added values of Aβ17, Aβ40 and Aβ42 peptides levels bound to cells in a blood sample from said subject sample;
(b) the ratio value between the Aβ17 peptide level bound to cells in a blood sample of the subject and the Aβ42 peptide level bound to cells in a blood sample of said subject;
(c) the ratio value between two parameters, wherein the first parameter corresponds to the added values of Aβ17 total peptide level in a plasma sample from said subject and the level of Aβ17 peptide bound to cells in a blood sample and the second parameter corresponds to the added values of Aβ42 total peptide level in a plasma sample from said subject and the level of Aβ42 peptide bound to cells in a blood sample;
(d) the ratio value between two parameters, wherein the first parameter corresponds to the level of Aβ17 peptide bound to cells in a blood sample and the second parameter corresponds to the added values of the Aβ40 and Aβ42 peptides levels bound to cells in a blood sample;
(e) the ratio value between two parameters, wherein the first parameter corresponds to the added values of the Aβ17 total peptide level in a plasma sample from said subject and the Aβ17 peptide level bound to cells in a blood sample and the second parameter corresponds to the added values of Aβ40 and Aβ42 total peptides levels in a plasma sample and of Aβ40 and Aβ42 peptide levels bound to cells in a blood sample;
wherein if the value of (a) is increased and/or the value of one or more of said parameters (b), (c), (d) and (e) is decreased with respect to the value of a reference sample of a subject suffering from MCI with non-prodromal Alzheimer's disease, the subject is suffering from MCI with prodromal Alzheimer's disease.

Therefore, the parameters to be measured that allow the distinction between a subject suffering from MCI with non-prodromal Alzheimer's disease and a subject suffering from MCI with prodromal Alzheimer's disease are the following:
(a) CB Aβ17+CB Aβ40+CB Aβ42
(b) CB Aβ17/CB Aβ42
(c) (TP Aβ17+CB Aβ17)/(TP Aβ42+CB Aβ42)
(d) CB Aβ17/(CB Aβ40+CB Aβ42)
(e) (TP Aβ17+CB Aβ17)/(TP Aβ40+TP Aβ42)+(CB Aβ40+CB Aβ42)

In another aspect, the invention relates to a method for distinguishing a subject suffering from MCI with non-prodromal Alzheimer's disease from a subject suffering from mild Alzheimer's disease comprising determining the value of one or more parameters selected from the group of:
(a) the added values of the Aβ17, Aβ40 and Aβ42 peptides levels bound to cells in a blood sample;
(b) the added values of the Aβ17, Aβ40 and Aβ42 total peptides levels in a plasma sample and the levels of the Aβ17, Aβ40 and Aβ42 peptides bound to cells in a blood sample;
(c) the added values of total Aβ42 peptide in a plasma sample and the level of Aβ42 peptide bound to cells in a blood sample;
(d) the added values of the total Aβ40 and Aβ42 peptides levels in a plasma sample and the levels of the Aβ40 and Aβ42 peptides bound to cells in a blood sample;
(e) the added values of total Aβ40 peptide level in a plasma sample and the level of Aβ40 peptide bound to cells in a blood sample;
(f) the ratio value between two parameters, wherein the first parameter corresponds to the level of the Aβ17 peptide bound to cells in a blood sample and the second parameter corresponds to the added values of the levels of Aβ40 and Aβ42 peptides bound to cells in a blood sample; and
(g) the ratio value between the level of the Aβ17 peptide free in a plasma sample and the Aβ17 peptide level bound to cells in a blood sample;
wherein if the value of one or more of said parameters is increased with respect to the value of a reference sample of a subject with MCI with non-prodromal Alzheimer's disease, the subject is suffering from mild Alzheimer's disease.

Therefore, the parameters to be measured for the distinction of a subject suffering from MCI with non-prodromal Alzheimer's disease from a subject suffering from mild Alzheimer's disease are the following:
(a) CB Aβ17+CB Aβ40+CB Aβ42
(b) (TP Aβ17+TP Aβ40+TP Aβ42)+(CB Aβ17+CB Aβ40+CB Aβ42)
(c) TP Aβ42+CB Aβ42
(d) (TP Aβ40+TP Aβ42)+(CB Aβ40+CB Aβ42)
(e) TP Aβ40+CB Aβ40
(f) CB Aβ17/(CB Aβ40+CB Aβ42)
(g) FP Aβ17/CB Aβ17

In another aspect, the invention relates to a method for distinguishing a subject suffering from MCI with prodromal Alzheimer's disease from a subject suffering from mild Alzheimer's disease comprising determining the value of one or more parameters selected from the group of:
(a) the ratio value between the Aβ17 peptide level free in a plasma sample and the level of the Aβ40 peptide free in a plasma sample; and
(b) the ratio value between two parameters, wherein the first parameter corresponds to the level of the Aβ17 peptide free in a plasma sample and the second parameter corresponds to the level of the Aβ40 and Aβ42 peptides free in a plasma sample;
wherein if the value of one or more of said parameters is increased with respect to the value of a reference sample of a subject with MCI with prodromal Alzheimer's disease, the subject is suffering from mild Alzheimer's disease.

Therefore, the parameters to be measured for the distinction between a subject suffering from MCI with prodromal Alzheimer's disease and a subject suffering from mild Alzheimer's disease are the following:
(a) FP Aβ17/FP Aβ40
(b) FP Aβ17/FP Aβ40+FP Aβ42

The term "diagnosis" as used herein includes the assessment of a subject's susceptibility to a disease, determination as to whether a subject presently has the disease, and also the prognosis of a subject affected by the disease. As will be understood by persons skilled in the art, such assessment normally may not be correct for 100% of the subjects to be diagnosed, although it preferably is correct. The term, however, requires that a statistically significant part of the subjects can be identified as suffering from the disease or having a predisposition thereto. If a part is statistically significant it can be determined simply by the person skilled in the art using several well known statistical evaluation tools, for example, determination of confidence intervals, determination of p values, Student's t-test, Mann-Whitney test, etc. Details are provided in Dowdy and Wearden, Statistics for Research, John Wiley & Sons, New York 1983. The preferred confidence intervals are at least 50%, at least 60%, at least 70%, at least 80%, at least 90%, at least 95%. The p values are preferably 0.2, 0.1 or 0.05.

As used herein, the term "subject" relates to all the animals classified as mammals and includes but is not limited to domestic and farm animals, primates and humans, for example, human beings, non-human primates, cows, horses, pigs, sheep, goats, dogs, cats, or rodents. Preferably, the subject is a male or female human being of any age or race.

The term "Alzheimer's Disease" (or "senile dementia") refers to a mental deterioration associated with specific degenerative brain disease that is characterized by senile plaques, neuritic tangles, and progressive neuronal loss which manifests clinically in progressive memory deficits, confusion, behavioral problems, inability to care for oneself, gradual physical deterioration and, ultimately, death.

The expression "mild Alzheimer's disease", in the context of the present invention, refers to a early stage of the Alzheimer's disease, wherein the subject experiences:
  Memory loss for recent events.
  Difficulty with problem solving, complex tasks and sound judgments.
  Changes in personality.
  Difficulty organizing and expressing thoughts.
  Getting lost or misplacing belongings.

Patients suffering mild Alzheimer's disease are identified using the NINCDS-ADRDA criteria (CDR=1, MMSE between 16 and 24 points and Medial temporal atrophy (determined by MRI)>3 points in Scheltens scale.

The term "mild cognitive impairment" or MCI refers to a transitional stage of cognitive impairment between normal aging and early Alzheimer's disease. Patients are usually identified as having MCI if they fulfill the Mayo Clinic criteria (CDR=0.5, they show a medial temporal atrophy (determined by MRI) which is higher than 3 points in Scheltens scale, they show a pattern of parietal and/or temporal hypometabolism in Positron Emission Tomography with 18-fluorodeoxyglucose (PET-FDG) (suggestive of AD).

The expression "prodromal Alzheimer's disease", also known as "MCI with probable Alzheimer's disease" refers to patients showing MCI and who are considered as showing high risk for conversion to Alzheimer's disease. Criteria for identifying a patient as probable AD are those as defined by the NINCDS-ADRDA criteria (McKhann G. et al., 1984, *Neurology*, 34:939-44), namely, dementia established by clinical and neuropsychological examination, progressive cognitive impairment present in two or more areas of cognition, onset of the deficits between the ages of 40 and 90 years and absence of other diseases capable of producing a dementia syndrome.

The expression "non-prodromal Alzheimer's disease", also known as "MCI with possible Alzheimer's disease" refers to patients showing MCI and who are considered as showing low risk of developing Alzheimer's disease. Criteria for identifying a patient as possible AD are those as defined as defined by the NINCDS-ADRDA criteria (McKhann G. et al., 1984, *Neurology*, 34:939-44), namely, dementia syndrome with an atypical onset, presentation or progression and without a known etiology but no co-morbid diseases capable of producing dementia are believed to be in the origin of it.

The term "healthy subject", as used in the present invention, refers to a subject in good health. In a preferred embodiment, said subject is older than 65 years old. It corresponds to a subject not suffering from a neurodegenerative disease or without any history of neurodegenerative disease. Preferably, the healthy subjects are patients who show an absence of memory complains, normal performance in neuropsychological tests and absence of structural alterations in MRI. A healthy subject may be healthy and have no other disease, or they may have a disease other than MCI and AD.

The term "distinguishing a healthy subject from a subject suffering from prodromal Alzheimer's disease" refers to the capability of discriminating between a subject not having symptoms of Alzheimer's disease (AD) and a subject suffering from prodromal Alzheimer's disease.

The term "distinguishing a healthy subject from a subject suffering from mild Alzheimer's disease" refers to the capability of discriminating between a subject not having symptoms of Alzheimer's disease (AD) and a subject in the early stages of AD (mild Alzheimer's disease).

The term "distinguishing a subject suffering from non-prodromal MCI from a subject suffering from a subject suffering from prodromal Alzheimer's disease" refers to the capability of discriminating between a subject having symptoms of non-prodromal MCI and a subject suffering from prodromal Alzheimer's disease.

The term "distinguishing a subject suffering from non-prodromal MCI from a subject suffering from mild Alzheimer's disease" refers to the capability of discriminating between a subject having symptoms of non-prodromal MCI and a subject in the early stages of AD (mild Alzheimer's disease).

The term "distinguishing a subject suffering from prodromal AD from a subject suffering from mild Alzheimer's disease" refers to the capability of discriminating between a subject having symptoms of prodromal AD and a subject in the early stages of AD (mild Alzheimer's disease).

The term "plasma" refers to the fluid component of the whole blood. Depending on the separation method used, plasma may be completely free of cellular components, or may contain various amounts of platelets and/or small amount of other cellular components.

The terms "levels of Aβ17, Aβ40 or Aβ42 peptides bound to cells" (hereinafter known as CB Aβ17, CB Aβ40 or CB Aβ42, respectively), as used herein, refers to amyloid beta peptides which are non-covalently associated to the surface of the cells present in the biological sample and which are unavailable for binding to antibodies added to the sample and hence, immunologically detectable. Typically, if the biological sample is blood, the amyloid beta peptide is associated to red blood cells, white blood cells, including neutrophils, eosinophils, basophils, lymphocytes and monocytes, and platelets. The amount of amyloid beta peptide associated to cells in a given sample can be determined and this value can be used alone or in combination with other parameters related to amyloid beta peptides in the methods of the invention. For this purpose, it is first required to isolate the cellular fraction from the biological sample. This can be carried out using any technique known to the skilled person such as centrifugation, sedimentation, filtration and the like. Once the cell fraction of a biological sample has been isolated, the cells are contacted with a protein solubilising agent.

The amount of amyloid beta peptide associated to cells in a given sample can be determined and this value can be used alone or in combination with other parameters related to amyloid beta peptides in the methods of the invention. For this purpose, it is first required to isolate the cellular fraction from the biological sample. This can be carried out using any technique known to the skilled person such as centrifugation, sedimentation, filtration and the like. Once the cell fraction of a biological sample has been isolated, the cells are contacted with a protein solubilising agent.

Suitable protein solubilising agents include detergents, chaotropic agents and reducing agents as defined below and are usually provided in a buffer solution at an adequate concentration. Suitable agents, buffer solutions and concentrations of agents in the buffer solution have been described below. The contacting step is carried out essentially as explained below in the method for releasing the amyloid peptide which is attached to components (proteins and lipids) of the biological sample. In a preferred embodiment, the protein solubilising agent is a detergent. In a still more preferred embodiment, the detergent is Tween 20. Suitable concentrations of Tween 20 for use as protein solubilising agent are as defined above, i.e. between 0.004-0.02%, more preferably of 0.005-0.01% (w/v).

The contacting step is carried out preferably at a low temperature in order to inhibit proteolytic activities present in the sample. Suitable temperatures are of about 0-10° C., preferably of about 3-5° C., e.g., about 4° C.

Typically, the contacting step is carried out by resuspending the cellular fraction in the biological sample with the solution comprising the protein solubilising agent. Said resuspension can be carried out by gentle pippeting up- and down, by stirring, preferably by shaking, more preferably by high speed shaking, most preferably by vortexing for at least 5 seconds, preferably for at least 10 seconds, more preferably for at least 15 seconds (e.g., for 15-50 seconds). Advantageous speeds for said mixing, stirring, shaking, high speed shaking or vortexing comprise a speed of at least 250 rpm, preferably of at least 500 rpm, more preferably of at least 1,000 rpm, most preferably of about 2,000-2,500 rpm.

The contacting step is carried out under conditions adequate for achieving partial or, preferably, full dissociation of the amyloid beta peptide from the cells present in the biological sample. The conditions can be adequately determined by one of ordinary skills in the art by monitoring the amount of amyloid beta peptide which is detectable before the contacting step and progressively at different time points after the contacting step has taken place.

The term "total Aβ peptide in plasma" (hereinafter known as TP Aβ17, TP Aβ40 or TP Aβ42), as used herein, refers to "Aβ peptide free in plasma" plus the "amyloid beta peptide associated to macromolecular components". The term "amyloid beta peptide associated to macromolecular components", as used herein, refers to the amyloid beta peptide which is non-covalently bound or attached to molecules found in the biological sample under study. This peptide is usually not readily accessible for immunological detection and thus, requires a pretreatment of the biological sample in order to achieve the separation of the peptide from the components. Under these conditions, the amyloid beta peptide attached to macromolecular components will be released from said components and will become available for immunological detection using specific antibodies. Since the biological sample contains already a certain amount of free amyloid beta peptide, the total amount of free amyloid peptide after contacting the sample with the protein solubilising agent will be the aggregate level of free amyloid beta peptide originally present and the level of amyloid beta peptide which has been released upon treatment with the protein solubilising agent. In case the level of amyloid beta peptide associated to macromolecular components present in the biological sample needs to be determined, this can be typically done by determining the level of free amyloid beta peptide prior to the treatment with the protein solubilising agent and the level of free amyloid beta peptide after the treatment with the protein solubilising agent and substracting the first value from the second value. For the purposes of the present invention, it is usually adequate to determine the aggregated level of free amyloid beta peptides which includes the originally free amyloid beta peptides as well as the level of amyloid beta peptides which have been released from the macromolecular components after the treatment with the protein solubilising agent. Therefore, the parameter which is usually determined when the sample is treated so as to dissociate the amyloid peptide from macromolecular components corresponds to the addition of the free peptide present in the sample and the peptide associated to macromolecular components.

The macromolecular components of the sample which may bind amyloid beta peptides and which contribute to the pool of amyloid beta peptide associated to macromolecular components includes both proteins as well as lipids. In the particular case that the method is carried out in blood or plasma samples, the macromolecular components include, without limitation, blood proteins and lipids. Exemplary blood proteins include albumin, immunoglobulin G, immunoglobulin E, immunoglobulin M, immunoglobulin A, fibrinogen (fibrin and degradation products thereof), alpha-1 antitrypsin, prealbumin, alpha-1 acid glycoprotein, alpha-1 fetoprotein, alpha-2 haptoglobin, macroglobulin, ceruloplasmin, transferring, C3/C4 Beta 2 microglobulin, beta lipoprotein, alpha, beta and gamma globulins, C-reactive protein (CRP), prothrombin, thyroxine-binding protein, transthyretin and the like. Exemplary blood lipids include free fatty acids, cholesterol, triglycerides, phospholipids, sphingolipids and the like.

The amount of amyloid beta peptide associated to macromolecular components can be determined by contacting a cell-free sample of the biological sample with a protein solubilising agent under conditions adequate for inducing the release of said amyloid beta peptides from the macromolecular components.

By contacting, it is meant herein adding to the sample a sufficient amount of a solution comprising the protein solubilising agent so that the concentration of the protein solubilising agent in the mixture is sufficient to effectively solubilise the amyloid beta peptide which is bound to the proteins and cells in the sample. Preferably, the protein solubilising agent is found in solution in a buffer solution so that the addition of the protein solubilising agent does not result in a substantial modification in the pH of the sample.

The term "protein solubilising agent", as used herein, refers to any compound of composition capable of altering the secondary, tertiary and/or quaternary structure of polypeptides while leaving the primary structure intact. By virtue of these properties, protein solubilising agents are capable increasing the solubility of proteins in a sample as well as of preventing inter- and intramolecular aggregation of proteins. Proteins solubilising agents suitable for use in the present invention include, without limitation, detergents, chaotropic agents, reducing agents or mixtures thereof.

The term "detergent", as used herein, is a synonym used for surfactants in general, and refers to amphipathic surface-active agents that, when added to a liquid, reduce surface tension of the liquid in comparison to the same liquid in the absence of the detergent. Detergents are also capable of preventing aggregation of proteins and of preventing non-specific interaction or binding of contaminants to a protein of interest. Detergents suitable for use in the present invention include, without limitation, non-ionic (neutral), anionic, cationic, or zwitterionic detergents.

Examples of non-ionic or neutral detergents include, without limitation, detergents of the Tween series, such as Tween® 20, Tween® 21, Tween® 40, Tween® 60, Tween® 61, Tween® 65, Tween® 80, Tween® 81, Tween® 85, detergents of the Span® series, such as Span® 20; detergents of the Tergitol series, such as Tergitol Type 15-S-12; detergents of the Brij® series, such as Brij® 35, Brij® 56, Brij® 72, Brij® 76, Brij® 92V, Brij® 97, Brij® 58P; detergents of the Triton® series, such as Triton® X-100, Triton® X-114, Triton® CF-21, Triton® CF-32, Triton® DF-12, Triton® DF-16, Triton® GR-5M, Triton® X-102, Triton® X-15, Triton® X-151, Triton® X-207, Triton® X-165, Triton® X-305, Triton® X-405, Triton® X-45, Triton® X-705-70, or a non-ionic conservative variant of at least one of said detergent.

Examples of anionic detergents include, without limitation, cholic acid and derivatives thereof, taurocholic acid, Triton X-200, Triton W-30, Triton-30, Triton-770, dioctyl sulfo succinate, $N_5N$-dimethyldodecylamine N-oxide, sodium 1-alkylsulfonates, N-lauroylsarcosine or fatty acid salts.

Examples of cationic detergents includes, without limitation, mono and di-methyl fatty amines, alkyl trimethyl ammonium salts, dialkyl dimethyl ammonium salts, alkyl amine acetates, trialkylammonium acetates, alkyldimethylbenzyl ammonium salts, dialkymethylbenzyl ammonium salts, alkylpyridinium halide and alkyl (alkyl substituted) pyridinium salts, alkylthiomethylpyridinium salts, alkylamidomethylpyridinium salts, alkylquinolinium salts, alkylisoquinolinium salts, N,N-alkylmethylpyrollidonium salts, 1,1-dialkylpiperidinium salts, 4,4-dialkylthiamorpholinium salts, 4,4-dialkylthiamorpholinium-1-oxide salts, methyl his (alkyl ethyl)-2-alkyl imidazolinium methyl sulfate (and other salts), methyl bis(alkylamido ethyl)-2-hydroxyethyl ammonium methyl sulfate (and other salts), alkylamidopropyl-dimethylbenzyl ammonium salts, carboxyalkyl-alkyldimethyl ammonium salts, alkylamine oxides, alkyldimethyl amine oxides, poly(vinylmethylpyridinium) salts, poly(vinylpyridine) salts, polyethyleneimines, trialkyl phosphonium bicarbonates (and other salts), trialkylmethyl phosphonium salts, alkylethylmethylsulfonium salts, and alkyldimethylsulfoxonium salts.

Examples of zwitterionic detergents include, without limitation, 3-[(3-cholamidopropyl)dimethylammonio]-1-propanesulfonate (CHAPS); 3-[(3-cholamidopropyl)dimethylammonio]-2-hydroxy-1-rhoropanesulfonate (CHAPSO); N-(alkyl C10-C16)-N,N-dimethylglycine betaine (EMPIGEN BB); Caprylyl sulfobetaine (SB3-10); 3-[N,N-dimethyl (3-myristoylaminopropyl)ammonio]propanesulfonate (Amidosulfobetaine-14; ASB-14); N-tetradecyl-N,N-dimethyl-3-ammonio-1-propoanesulfonate(3-14 Detergent; ZWITTERGENT); N-do de cyl-N,N'-dimethyl-3-ammonio-1-propanesulfonate; N-octadecyl-N,N-dimethyl-3-ammonio-1-propanesulfonate; N-decyl-N,N-dimethyl-3-ammonium-1-propanesulfonate; Mirataine CB; Mirataine BB; Mirataine CBR; Mirataine ACS; Miracare 2 MHT and Miracare 2MCA.

In a preferred embodiment, the protein solubilising reagent is a detergent. In a still more preferred embodiment, the detergent is Tween 20. In a still more preferred embodiment, Tween 20 is used at a concentration of 0.5%.

A "chaotropic agent", as used herein, relate to a compound or mixture of compounds which disrupt hydrogen bonds and hydrophobic interactions both between and within proteins. When used at high concentrations, chaotropic agents disrupt secondary protein structure and bring into solution proteins that are not otherwise soluble. Suitable chaotropic agents include, without limitation, urea, guanidinium isothiocyanate, sodium thiocyanate (NaSCN), Guanidine HCl, guanidinium chloride, guanidinium thiocyanate, lithium tetrachloroacetate, sodium perchlorate, rubidium tetrachloroacetate, potassium iodide or cesium trifluoroacetate.

The term "reducing agent", as used herein, refers to any compound or material which maintains sulfhydryl groups in the reduced state and reduces intra- or intermolecular disulfide bonds. By way of example, reducing agents suitable for the method of the present invention include both sulfhydryl or phosphine reducing agents. Examples of sulfhydryl reductants include dithiothreitol (DTT), dithioerythritol (DTE), and β-mercaptoethanol. Examples of phosphine reductants include tributylphosphine (TBP) and tris-carboxyethylphosphine (TCEP).

Typically, the biological sample is first processed to remove the cellular fraction. The cell-free sample is then contacted with the protein solubilising agent. In a preferred embodiment, the sample is diluted using a buffer comprising the protein solubilising agent. Typically, the sample is diluted 5-fold in a buffer solution comprising Tween 20.

As used herein, a "buffer solution" is any substance or mixture of compounds in solution that is capable of neutralizing both acids and bases without appreciably changing the original acidity or alkalinity of the solution. Suitable buffer solutions to be used in the method of the invention include, without limitation, Tris buffer solution, phosphate buffer solution, borate buffer solution, carbonate buffer solution, glycine-sodium hydroxide buffer solution, or the like. Preferably, the buffer solution is a phosphate buffer solution such as phosphate-buffered saline or PBS.

The amount of solution comprising the protein solubilising agent which is added to the biological sample is not essential as long as sufficient dissociation of the amyloid beta peptide is achieved. By way of example, the biological fluid may be diluted in the solution comprising the protein solubilising agent at a dilution of at least 1/2 (v/v), 1/3 (v/v), 1/4 (v/v), 1/5 (v/v), 1/6 (v/v), 1/7 (v/v), 1/8 (v/v), 1/9 (v/v), 1/10 (v/v), 1/20 (v/v), 1/50 (v/v), 1/60 (v/v), 1/80 (v/v), 1/90 (v/v), 1/100 (v/v) or more. The skilled person will appreciate that any combination of said dilution rates and of said protein solubilising agent concentration can be used as long as the final concentration of protein solubilising agent is adequate for achieving the desired effect. For instance, the solution containing the protein solubilising agent may comprise said selected protein solubilising agent (s) at a concentration ranging from 0.001% to 0.5% (w/v). After having been diluted in said solution containing the protein solubilising agent, said biological fluid typically contains said surfactant(s) at less than 0.1% (w/v), preferably less than 0.6% (w/v), more preferably no more than 0.5% (w/v), most preferably no more than 0.45% (w/v) and even most preferably 0.5%.

Suitable buffer systems for use in the present invention include Tris-HCl buffers including a salt such as NaCl or KCl and, optionally, BSA. Particular buffer systems include, without limitation, 50 mM Tris-HCl pH 8, 0.5M NaCl, 0.05% BSA, 0.05% Tween-20;
50 mM Tris-HCl pH 8, 0.5M NaCl, 0.05% BSA, 0.05% Tween-20, 1M GuHCl;
50 mM Tris-HCl pH 8, 0.5M KCl, 0.05% BSA, 0.05% Tween-20;
50 mM Tris-HCl pH 8, 0.5M KCl, 0.05% BSA, 0.05% Tween-20, 1M GuHCl;

50 mM Tris-HCl pH 8, 0.5M NaCl, 0.05% BSA, 0.05% Tween-80;
50 mM Tris-HCl pH 8, 0.5M KCl, 0.05% BSA, 0.05% Tween-80;
50 mM Tris-HCl pH 8, 0.5M NaCl; 0.05% BSA, 0.05% Triton X-100
50 mM Tris-HCl pH 8, 0.5M KCl, 0.05% BSA, 0.05% Triton X-100;
50 mM Tris-HCl pH 8; 0.05% BSA, 0.05% Tween-20;
50 mM Tris-HCl pH 8, 0.5M NaCl, 0.1% BSA, 0.05% Tween-20;
50 mM Tris-HCl pH 8, 0.5M NaCl, 0.05% BSA, 0.1% Tween-20;
50 mM Tris-HCl pH 8, 0.5M NaCl, 0.1% BSA, 0.1% Tween-20;
50 mM Tris-HCl pH 8, 1M NaCl, 0.05% BSA, 0.05% Tween-20;
50 mM Tris-HCl pH 8, 1.5M NaCl, 0.05% BSA, 0.05% Tween-20;
50 mM Tris-HCl pH 8, 2M NaCl, 0.05% BSA, 0.05% Tween-20;
50 mM Tris-HCl pH 8, 2.5M NaCl, 0.05% BSA, 0.05% Tween-20;
50 mM Tris-HCl pH 8, 3M NaCl, 0.05% BSA, 0.05% Tween-20;
50 mM Tris-HCl pH 8, 0.5M NaCl, 0.05% BSA, 0.05% Tween-20, 10% DMSO;
50 mM Tris-HCl pH 8, 0.5M NaCl, 0.05% BSA, 0.05% Tween-20, 0.5 M GuHCl;
50 mM Tris-HCl pH 6, 0.5M NaCl, 0.05% BSA, 0.05% Tween-20;
50 mM Tris-HCl pH 7, 0.5M NaCl, 0.05% BSA, 0.05% Tween-20;
50 mM Tris-HCl pH 9, 0.5M NaCl, 0.05% BSA, 0.05% Tween-20;
50 mM Tris-HCl pH 8, 0.5M NaCl, 0.05% BSA For example, when Tween 20 is used as a protein solubilising agent, the preferred concentration is of 0.004-0.02%, more preferably of 0.005-0.01% (w/v).

The contacting step is carried out preferably at a low temperature in order to inhibit proteolytic activities present in the sample. Suitable temperatures are of about 0-10° C., preferably of about 3-5° C., e.g., about 4° C.

Once the biological fluid has been contacted with the solution comprising the protein solubilising agent, both fluids may be mixed. Mixing may be carried out by stirring, preferably by shaking, more preferably by high speed shaking, most preferably by vortexing for at least 5 seconds, preferably for at least 10 seconds, more preferably for at least 15 seconds (e.g., for 15-50 seconds). Advantageous speeds for said mixing, stirring, shaking, high speed shaking or vortexing comprise a speed of at least 250 rpm, preferably of at least 500 rpm, more preferably of at least 1,000 rpm, most preferably of about 2,000-2,500 rpm.

The contacting step is carried out under conditions adequate for achieving partial or, preferably, full dissociation of the amyloid beta peptide from the protein and lipids present in the biological sample. The conditions can be adequately determined by one of ordinary skills in the art by monitoring the amount of amyloid beta peptide which is detectable before the contacting step and progressively at different time points after the contacting step has taken place. The time course experiment may be determined as described in example of the experimental part.

The skilled person will appreciate that when the level of amyloid beta peptide is determined by diluting a biological sample with a buffer containing the protein solubilising reagent, the level of free amyloid beta peptide obtained by immunological determination will have to be corrected in order to take into consideration the dilution factor previously applied to the biological sample.

The terms "A$\beta$17, A$\beta$40 or A$\beta$42 peptides free in plasma" (hereinafter known as FP A$\beta$17, FP A$\beta$40 or FP A$\beta$42, respectively), as used herein, refer to the level of amyloid beta peptides which are not associated to any component of the biological sample and which is readily available for binding to a specific antibody. This peptide may be determined by conventional immunological techniques by contacting the biological sample with an antibody specific for said peptide. In a preferred embodiment, the level of free amyloid peptide is determined in plasma.

The term "reference value", as used herein, refers to a value of the parameter which is being used for comparison and which has been determined in a subject not suffering from a neurodegenerative disease or without any history of neurodegenerative disease. Preferably, the subjects from whom the reference values for the different parameters and calculated parameters are obtained are patients showing an absence of memory complains, normal performance in neuropsychological tests and absence of structural alterations in MRI.

In particular, reference values are selected which allow a sensitivity higher than 85% and a specificity higher than 75%. In another preferred embodiment, the reference values are selected so as to obtain a sensitivity higher than 70% and an specificity higher than 70%. Preferably, the reference values allow obtaining a prediction with an accuracy or precision of at least 80%.

Once the value of the parameter is determined, the determination of whether a subject is suffering from mild Alzheimer's disease is carried out when there is an alteration in the value of the parameter or in the value of the calculated parameter with respect to the reference value.

Any method suitable for the determination of peptides can be used in the present invention. By way of example, the concentration of amyloid beta peptide can be determined using one or more techniques chosen from Western blot, immunoprecipitation, enzyme-linked immunosorbent assay (ELISA), surface plasmon resonance, precipitin reaction, a gel diffusion immunodiffusion assay, radioimmunoassay (RIA), fluorescent activated cell sorting (FACS), two-dimensional gel electrophoresis, capillary electrophoresis, mass spectroscopy (MS), matrix-assisted laser desorption/ionization-time of flight-MS (MALDI-TOF), surface-enhanced laser desorption/ionization-time of flight (SELDI-TOF), high performance liquid chromatography (HPLC), fast protein liquid chromatography (FPLC), multidimensional liquid chromatography (LC) followed by tandem mass spectrometry (MS/MS), thin-layer chromatography, protein chip expression analysis and laser densiometry.

In a preferred embodiment, the determination of the method of the invention is carried out by an immunological method. As used herein, "immunological method", when applied to a determination, relates to any method which involves the use of one or more antibodies specific for a target substance in order to determine the amount/concentration of said target substance excluding other substances found in the sample. Suitable immunological methods include, without limitation, Western blot, immunoprecipitation, enzyme-linked immunosorbent assay (ELISA), surface plasmon resonance, radioimmunoassay (RIA). In a preferred embodiment, the determination or detection of the amyloid beta peptide is carried out by ELISA.

The skilled person will appreciate that any type of antibody is adequate for performing the immunological detection methods according to the invention provided that the antibody is specific enough to effectively discriminate the amyloid beta peptide species in the sample from other substances.

The term "ELISA", as used herein, stands for enzyme-linked immunosorbent assay and relates to an assay by which an unknown amount of target substance (the amyloid beta peptide) is affixed to a surface, and then a specific antibody is washed over the surface so that it can bind to the antigen. This antibody is linked to an enzyme, and in the final step a substance is added that the enzyme can convert to some detectable signal. Different types of ELISA assays are known and can be applied to the method of the invention, including direct ELISA, sandwich ELISA, competitive ELISA and ELISA reverse method & device (ELISA-R m&d).

Direct ELISA is carried out by contacting the test sample comprising the amyloid beta peptide with a solid support which has been previously coated with a concentrated solution of a non-interacting protein or reagent (bovine serum albumin, casein). Once the amyloid beta peptide present in the test sample is absorbed onto the support, an antibody specific for amyloid beta peptide is added under conditions adequate for binding onto the amyloid beta peptide. The antibody which is bound is then detected with a secondary antibody which is coupled to a detectable tag or to a substrate modifying enzyme. The signal resulting from the detectable tag or from the substrate is then proportional to the amount of antibody bound to the support which, in turn, correlates directly with the amount of amyloid beta peptide in the sample.

Competitive ELISA assay includes a first step wherein the test sample comprising an unknown amount of amyloid beta peptide is contacted with a first antibody as defined above. The antibody-antigen complexes are added to an antigen coated well. Once the support is washed to remove any non-specifically bound complexes, the amount of first antibody is detected with a second antibody which is coupled to a detectable moiety. In this type of assays, the higher the original antigen concentration, the weaker the eventual signal. An alternative competitive ELISA assay is that which includes an enzyme-linked antigen rather than enzyme-linked antibody. The labeled antigen competes for primary antibody binding sites with the sample antigen (unlabeled). Using this type of assays, the concentration of antigen in the sample results inversely correlates with the amount of labeled antigen retained in the well and, accordingly, in a weaker signal.

The reverse ELISA method & device (ELISA-R m&d) uses an innovative solid phase constituted of an immunosorbent polystyrene rod with 4-12 protruding ogives; the entire device is suitable to be introduced in a test tube containing the collected sample and the following steps (washing, incubation in conjugate and incubation in chromogenous) are easily carried out by immerging the ogives in microwells of standard microplates pre-filled with reagents, sealed and stored until their use.

In a preferred embodiment, the ELISA assay is an ELISA sandwich assay. The ELISA sandwich assay involves coating a support with a first antibody specific for amyloid beta peptide, applying the sample containing the amyloid beta peptide which will result in the binding of the amyloid beta peptide to the first antibody and applying a second antibody also specific for amyloid beta peptide, wherein said second antibody is usually coupled to a detectable tag or to a substrate-modifying enzyme. The signal generated by the tag or by the converted substrate is the proportional to the amount of antigen in the sample.

It is preferred to carry out the different steps of the method using in parallel the samples to be determined and a number of reference samples having known concentrations of the compound which is to be determined. A standard curve for the Aβ17 peptide must be prepared using increasing concentrations for determining the concentrations of the parameters mentioned above. The standard curve serves the dual purpose of (i) establishing the concentration range wherein the signal increases linearly with the concentration of the target peptide and (ii) determining the concentration of the peptides in the test sample by interpolation of the signal obtained with the test or standard samples in the curve to obtain concentration values. In view of the high sensitivity of the assay of the invention, preferred concentrations of the test samples are e.g. 3.125; 6.25; 12.5; 25; 50; 100 and 200 pg/mL. It will be appreciated that the concentrations of the samples used for obtaining the standard curve will vary for each test substrate. However, determination of the linear range of the assay can be easily determined by the skilled practitioner by conventional means.

The term "alteration" refers to a statistically significant increase or decrease in the value of the parameter under consideration with respect to the reference value.

By "statistically significant", as used herein, relate to a statistical analysis of the probability that there is a non-random association between two or more results, endpoints or outcome, i.e. that there is a certain degree of mathematical assurance that the value of the parameter is associated with a particular patient population with respect to the reference value.

The statistical significance of the alteration in the values can be determined using p-value. For instance, when using p-value, a parameter is identified as showing a significant alteration when the p-value is less than 0.1, preferably less than 0.05, more preferably less than 0.01, even more preferably less than 0.005, the most preferably less than 0.001.

Typically, the value of the parameter under consideration can be assigned as being "increased" when the value above the reference value is of at least 1.1-fold, 1.5-fold, 5-fold, 10-fold, 20-fold, 30-fold, 40-fold, 50-fold, 60-fold, 70-fold, 80-fold, 90-fold, 100-fold or even more compared with the reference value. On the other hand, a parameter value can be considered as being "decreased" when it is at least 0.9-fold, 0.75-fold, 0.2-fold, 0.1-fold, 0.05-fold, 0.025-fold, 0.02-fold, 0.01-fold, 0.005-fold or even less compared with reference value. In a particular embodiment, the alteration in the value of the parameter or in the value of the calculated parameter with respect to the reference value is an increase.

Further embodiments of the invention are the following:

[1] An antibody which specifically binds to the Aβ(1-17) peptide.
[2] An antibody as defined in [1] which does not show substantial cross-reactivity towards a Aβ peptide selected from the group consisting of Aβ(1-15), Aβ(1-16), Aβ(1-38), Aβ(1-40), Aβ(1-42) and a combination of one or more of them.
[3] An antibody as defined in [1] or [2] which is a policlonal antibody.
[4] An antibody as defined in any of [1] to [3] wherein said antibody has been obtained using as immunogen a Aβ peptide selected from the group consisting of SEQ ID NO:1 or the SEQ ID NO:2.
[5] A kit for the detection of the Aβ(1-17) peptide, comprising:
(i) a first antibody which is an antibody as defined in any of [1] to [3] and
(ii) a second antibody which recognises a region of the Aβ(1-17) peptide different from the region that is recognised by the first antibody

[6] Kit according to [5] wherein the first or the second antibody is coupled to a first member of a binding pair;

[7] Kit according to [6] further comprising a second member of said binding pair wherein said second member of the binding pair is coupled to a detectable tag.

[8] Kit as defined in [7] wherein, if the detectable tag which is coupled to the second member of the binding pair is an enzyme tag, then the kit further comprises a substrate which can be converted by said enzyme into a detectable product.

[9] Kit as defined in any of [5] to [8] further comprising an antibody or a combination of antibodies which specifically bind to Aβ40 and/or Aβ42.

[10] Kit as defined in any of [5] to [9] further comprising a solid support.

[11] Kit as defined in [10] wherein the antibody which is not coupled to a first member of a binding pair is prebound to the solid support.

[12] Kit as defined in any of [5] to [11] further comprising a sample containing Aβ17, Aβ40 and/or Aβ42 peptides.

[13] A method for determining or detecting the Aβ(1-17) peptide in a sample comprising the steps of:
(i) capturing the Aβ(1-17) peptide present in the sample with a first antibody which binds specifically to said peptide,
(ii) contacting the immune complexes formed in step (i) with a second antibody, wherein said second antibody is as defined in any of [1] to [4] and wherein said second antibody recognises a different region than the first antibody and is coupled to a first member of a binding pair;
(iii) contacting the complexes formed in step (ii) with a second member of a binding pair which is coupled to a detectable tag, and
(iv) detecting or determining the activity or amount of the detectable tag.

[14] A method as defined in any of [13] to [17] wherein the biological sample is selected from the group of blood, serum, plasma and CSF.

[15] A kit as defined in any of [1] to [12] or a method as defined in [13] or [14] wherein the first antibody is a monoclonal antibody.

[16] A kit or a method as defined in [15] wherein the monoclonal antibody is the 6E10 antibody.

[17] A kit or method as defined in any of [1] to [16] wherein said first member of a binding pair is biotin and the second member of a binding pair is avidin, streptavidin or a functionally equivalent variant thereof

[18] A kit or method as defined in any of [1] to [17] wherein the detectable tag is a fluorescent molecule, a luminescent molecule or an enzyme.

[19] A method for the monitoring of a neurodegenerative disease in a subject, comprising:
(a) determining in a sample from said subject at a first time point the level of the Aβ17 peptide free in a plasma sample and the level of Aβ17 peptide bound to cells in a blood sample in a sample of said subject;
(b) determining in a sample from said subject at a second time point the level of the Aβ17 peptide free in a plasma sample and the level of Aβ17 peptide bound to cells in a blood sample in a sample of said subject and
(c) comparing the ratio of level of Aβ17 peptide free in a plasma sample and the level of Aβ17 peptide bound to cells in a blood sample at said first and second time points;

wherein if said ratio is increased at the second time point with respect to the first time point, it is indicative of a worsening of Alzheimer's disease in the subject between said first and said second time points.

[20] Method according to [19] wherein the neurodegenerative disease is Alzheimer's disease.

[21] Method according to any of [19] or [20] wherein the determination of the level of the Aβ17 peptide is carried out by ELISA.

[22] Method according to [21] wherein the determination of the level of the Aβ17 peptide levels is carried out using a method as defined in any of [13] to [18].

[23] A method for determining whether a subject is suffering from mild Alzheimer's disease comprising determining the value of one or more parameters selected from the group of consisting of:
(a) the added values of Aβ17, Aβ40 and Aβ42 peptides levels bound to cells in a blood sample from said subject sample;
(b) the added value of the Aβ17, Aβ40 and Aβ42 total peptides levels in a plasma sample from said subject and the Aβ17, Aβ40 and Aβ42 peptides levels bound to cells in a blood sample from said subject;
(c) the added value of total Aβ42 peptide level in a plasma sample from the subject and the level of Aβ42 peptide bound to cells in a blood sample from the subject;
(d) the added values of total Aβ40 and Aβ42 peptides levels in a plasma sample from the subject and the Aβ40 and Aβ42 peptides levels bound to cells in a blood sample from the subject; and
(e) the ratio value between the level of the Aβ17 free in a plasma sample from said subject and the Aβ17 peptide bound to cells in a blood sample from the subject;

wherein if the value of one or more of said parameters is increased with respect to the value of said parameters in a reference sample of a healthy subject, then the subject is suffering from mild Alzheimer's disease.

[24] A method for determining whether a subject suffers from MCI with prodromal Alzheimer's disease comprising determining the value of one or more parameters selected from the group of:
(a) the added values of the total Aβ42 peptide level in a plasma sample from said subject and the Aβ42 peptide level bound to cells in a blood sample of said subject;
(b) the added values of the total Aβ40 and Aβ42 peptides level in a plasma sample from the subject and the Aβ40 and Aβ42 peptides levels bound to cells in a blood sample from said subject;
(c) the ratio value between the level of the Aβ17 peptide free in a plasma sample from the subject and the level of Aβ17 peptide bound to cells in a blood sample from said subject;
(d) the ratio value between the level of Aβ17 peptide bound to cells in a blood sample and the level of Aβ42 peptide bound to cells in a blood sample;
(e) the ratio value between two parameters, wherein the first parameter corresponds to the added levels of total Aβ17 peptide in a plasma sample and the level of Aβ17 peptide bound to cells in a blood sample and the second parameter correspond to the added levels of total Aβ42 peptide in a plasma sample and the level of Aβ42 peptide bound to cells in a blood sample;
(f) the ratio value between two parameters, wherein the first parameter corresponds to the level of Aβ17 peptide bound to cells in a blood sample and the second parameter corresponds to the added value of the levels of the Aβ40 peptide bound to cells in a blood sample and of the Aβ42 peptide bound to cells in a blood sample; and (g) the ratio value between two parameters, wherein the first parameter corresponds to the added values of the level of total Aβ17 peptide in a plasma sample from said subject and the level of the Aβ17 peptide bound to cells in a blood sample and the second parameter corresponds to the added value of the total Aβ40 and Aβ42 peptides in a plasma sample and the levels of Aβ40 and Aβ42 peptides bound to cells in a blood sample;

wherein if the value of one or more of the parameters (a), (b) or (c) is increased and/or the value of one or more of the parameters (d), (e), (f) or (g) is decreased with respect to the value in a reference sample of a healthy subject, the subject is suffering from MCI with prodromal Alzheimer's disease.

[25] A method for distinguishing a subject suffering from MCI with non-prodromal Alzheimer's disease from a subject suffering from MCI with prodromal Alzheimer's disease comprising determining the value of one or more parameters selected from the group of:

(a) the added values of Aβ17, Aβ40 and Aβ42 peptides levels bound to cells in a blood sample from said subject sample;

(b) the ratio value between the Aβ17 peptide level bound to cells in a blood sample of the subject and the Aβ42 peptide level bound to cells in a blood sample of said subject;

(c) the ratio value between two parameters, wherein the first parameter corresponds to the added values of Aβ17 total peptide level in a plasma sample from said subject and the level of Aβ17 peptide bound to cells in a blood sample and the second parameter corresponds to the added values of Aβ42 total peptide level in a plasma sample from said subject and the level of Aβ42 peptide bound to cells in a blood sample;

(d) the ratio value between two parameters, wherein the first parameter corresponds to the level of Aβ17 peptide bound to cells in a blood sample and the second parameter corresponds to the added values of the Aβ40 and Aβ42 peptides levels bound to cells in a blood sample;

(e) the ratio value between two parameters, wherein the first parameter corresponds to the added values of the Aβ17 total peptide level in a plasma sample from said subject and the Aβ17 peptide level bound to cells in a blood sample and the second parameter corresponds to the added values of Aβ40 and Aβ42 total peptides levels in a plasma sample and of Aβ40 and Aβ42 peptide levels bound to cells in a blood sample;

wherein if the value of (a) is increased and/or the value of one or more of said parameters (b), (c), (d) and (e) is decreased with respect to the value of a reference sample of a subject suffering from MCI with non-prodromal Alzheimer's disease, the subject is suffering from MCI with prodromal Alzheimer's disease.

[26] A method for distinguishing a subject suffering from MCI with non-prodromal Alzheimer's disease from a subject suffering from mild Alzheimer's disease comprising determining the value of one or more parameters selected from the group of:

(a) the added values of the Aβ17, Aβ40 and Aβ42 peptides levels bound to cells in a blood sample;

(b) the added values of the Aβ17, Aβ40 and Aβ42 total peptides levels in a plasma sample and the levels of the Aβ17, Aβ40 and Aβ42 peptides bound to cells in a blood sample;

(c) the added values of total Aβ42 peptide in a plasma sample and the level of Aβ42 peptide bound to cells in a blood sample;

(d) the added values of the total Aβ40 and Aβ42 peptides levels in a plasma sample and the levels of the Aβ40 and Aβ42 peptides bound to cells in a blood sample;

(e) the added values of total Aβ40 peptide level in a plasma sample and the level of Aβ40 peptide bound to cells in a blood sample;

(f) the ratio value between two parameters, wherein the first parameter corresponds to the level of the Aβ17 peptide bound to cells in a blood sample and the second parameter corresponds to the added values of the levels of Aβ40 and Aβ42 peptides bound to cells in a blood sample; and (g) the ratio value between the level of the Aβ17 peptide free in a plasma sample and the Aβ17 peptide level bound to cells in a blood sample;

wherein if the value of one or more of said parameters is increased with respect to the value of a reference sample of a subject having MCI with non-prodromal Alzheimer's disease, the subject is suffering from mild Alzheimer's disease.

[27] A method for distinguishing a subject suffering from MCI with prodromal Alzheimer's disease from a subject suffering from mild Alzheimer's disease comprising determining the value of one or more parameters selected from the group of:

(a) the ratio value between the Aβ17 peptide level free in a plasma sample and the level of the Aβ40 peptide free in a plasma sample; and (b) the ratio between two parameters, wherein the first parameter corresponds to the level of the Aβ17 peptide free in a plasma sample and the second parameter corresponds to the added levels of the Aβ40 and Aβ42 peptides free in a plasma sample;

wherein if the value of one or more of said parameters is increased with respect to the value of a reference sample of a prodromal mild cognitive impairment subject, the subject is suffering from mild Alzheimer's disease.

[28] Method according to any of [23] to [27] wherein the determination of the level of one or more of the Aβ17, Aβ40 and Aβ42 peptides is determined by ELISA.

The following examples are provided as illustration and should not be construed as limiting the scope of the invention.

EXAMPLES

Example 1

Generation of the Anti-Aβ17 Antibody

Four rabbits were immunized with the following peptides VHHQKL, corresponding to Aβ(12-17) (SEQ ID NO:2) and EVHHQKL, corresponding to Aβ(11-17) (SEQ ID NO:3), two of them with the first peptide and two more rabbits with the second peptide. Both peptides contained in N-terminal an additional amino acid, a cysteine for conjugation.

The carrier used for conjugation was Keyhole limpet hemocyanin (KLH) (Pierce, ref. 77600). The conjugation was carried out with the crosslinker NHS-PEG$_4$-Maleimide (Pierce, ref 22104). As adjuvants, three types were used: Freund's Adjuvant Complete (Sigma, ref. F5881), Freund's Adjuvant Incomplete (Sigma, ref. F5506) and Imject Alum (Pierce, ref. 77161).

The immunization protocol was the following:
The four rabbits were immunized every week with 100 μg of the peptides.

The first dose was administered using Freund's Adjuvant Complete as adjuvant, followed by another dose with Freund's Adjuvant Incomplete and a third dose with Alum.

After the first three administrations, the antibody titer obtained was too low to allow purification. Thus, the dose was increased to 200 µg of the peptides in three more administrations, alternating the adjuvants: Freund's Adjuvant Incomplete-Alum-Freund's Adjuvant Incomplete.

The antibody titers obtained for the four rabbits were very high and purification was carried out by affinity chromatography (with the Aβ17 peptide).

A dot-blot was carried out to determine the specificity of the anti-Aβ17 antibody, wherein other Aβ peptides were included (FIG. 1). The anti-Aβ17 antibody was added in two dilutions (1:1000 and 1:2000) and the secondary antibody used was Goat anti-rabbit-HRP 1:2000. 500 ng of each peptide were loaded in 2.5 µl. The dot-blot was developed with ECL with the SNAP technology at 1 minute and 3 minutes exposition. As it is shown in said Figure, the antibody is highly specific for the Aβ17 peptide and it does not recognize specifically the Aβ15, Aβ16, Aβ38, Aβ40 and Aβ42.

Example 2

Determination of Aβ17 Peptide in Samples (1) Determination by Mass Spectrometry
Reagents Formic acid, sodium chloride, α-Cyano-4-hydroxycinnamic acid (α-CHCA), trifluoroacetic acid (TFA), DL-Dithiothreitol (DTT), triethanolamine, Tris and bovine serum albumin (BSA) were from Sigma (Steimheim, Germany). Acetonitrile was purchased from Carlo-Erba (Rodano, MI, Italy). Dimethyl pimelimidate.2HCl (DMP) was acquired from Pierce (Rockford, Ill., USA). Tricine sample buffer was purchased from Bio-Rad (Hercules, Calif., USA).

Immunoprecipitation (IP) Procedure

IP-MALDI procedure was carried out as described by Portelius et al. 2007 (J. Proteome. Res. 6 (11), 4433-4439), with some modifications in order to adapt the procedure to the analysis of dog samples. In first place, different amounts of Aβ specific antibodies were used (6E10 and 4G8-specific for Aβ epitopes in amino acids 4-9 and 18-22, respectively, Signet Laboratories, Inc., Dedham, Mass., USA) and SAR2 (specific for anti-Aβ40 carboxy terminal epitope, Araclon Biotech S.L., Zaragoza, Spain) in order to determine the optimum quantity of each antibody by Western-blotting. The optimization procedure involved different steps. Each antibody was separately added to 50 µL Dynabeads Protein G (Invitrogen Dynal AS, Oslo, Norway) according to the manufacturer's description. Beads were incubated with different amounts of antibody, washed, and then antibodies were eluted by boiling the beads in tricine sample buffer with DTT. The saturating amount of each antibody was determined by Western-blotting.

Furthermore, incubation time (1 hour and overnight) and temperature (4° C., room temperature and 37° C.) of the beads with the antibody and the complex beads-antibody with the samples were also optimized. Another optimized parameter was the elution condition (0.5, 2.5 and 5% formic acid, as well as several percentages of organic solvents, such as acetonitrile).

Two different protocols were applied during this study. The first one is basically based on the instructions of the manufacturer with the optimized parameters: an aliquot of the Aβ specific antibody (4 µg of 6E10 or 8 µg of 4G8 or 6 µg of SAR 2) was incubated with 50 $\mu$L of Dynabeads Protein G for 1 hour at room temperature in a rotary shaker. After that, three washes with Phosphate Buffer Saline (PBS: 1 mM $NaH_2PO_4$ $H_2O$, 5 mM $Na_2HPO_4.2H_2O$, 138 mM NaCl) were carried out. 1 mL of CSF was added and incubated overnight at room temperature in a rotary shaker. CSF was removed from the beads after incubation, with the help of a magnet (DynaMag-2 or DynaMag-15, Invitrogen Dynal AS, Oslo, Norway) and discarded. Beads were washed three times with 1 mL 100 mM Tris pH=6.8, and finally elution was carried out with 25 µL of 5% formic acid. The eluate was incubated 5 minutes at room temperature in a Thermomixer. The eluted compounds were desalted with ZipTip $C_{18}$ tips (Millipore, Billerica, Mass., USA). The ZipTip $C_{18}$ protocol consists of several steps: tips solvation with acetonitrile, conditioning with 0.1% TFA (repeating this step several times), sample load (by pipetting up and down several times), a wash step with 0.1% TFA and final elution with 3 µL of α-CHCA (5 mg/mL).

In the second protocol, citrate-phosphate buffer, pH=5.0 (24.5 mM citric acid, 52 mM $Na_2HPO_4.2H_2O$) was used for the wash and bind steps instead of PBS. Before elution, beads were washed with PBS instead of 100 mM Tris pH=6.8. This second protocol resulted in mass spectra with less background noise and more intense peaks and it was used for the rest of the experiments.

For immunoprecipitation of human samples, 50 µl of Dynabeads sheep anti-mouse (Invitrogen Dynal AS, Oslo, Norway) were used. Beads were washed three times with PBS and incubated with the optimized amount of the specific antibody (8 µg of 6E10 or 8 µg of 4G8) for 1 hour at room temperature in a rotary shaker. After that, the supernatant was eliminated and beads were washed with 1 mL of 0.2 M triethanolamine pH=8.2. Crosslinking reaction took place after the addition of 1 mL of 20 mM DMP (an homobifunctional crosslinking agent with amine reactive groups; (Greg T Hermanson, 2010) in 0.2 M triethanolamine pH=8.2. Beads and antibodies were incubated for 30 minutes at room temperature, then the supernatant was discarded and the reaction was stopped by addition of 1 mL of 50 mM Tris pH=7.5 for 15 minutes in a rotary shaker. The crosslinked beads were washed three times with 1 ml of PBS containing 0.1% of BSA. 1 mL of pooled human CSF was added and incubated overnight at room temperature. Supernatants were discarded and beads were washed several times with PBS. Aβ species were eluted with 25 µL of 5% of formic acid. The eluted compounds were desalted with ZipTip $C_{18}$ using the same protocol described above.

MALDI-TOF and MALDI-TOF/TOF Mass Spectrometry (MS).

0.7 µl of the eluted sample were placed directly on the MALDI target until complete evaporation. All the spectra were acquired with an ABI4800 MALDI-TOF/TOF mass spectrometer (AB/Sciex) equipped with a diode-pumped solid state Nd:YAG laser (355 nm) working at a 200 Hz repetition rate. For obtaining MS spectra the instrument was operated in reflector mode and all the experiments were carried out in positive ion mode. 400 nanoseconds after laser firing, an accelerating voltage of 20 kV was applied. Ions were refocused in the two-stage reflector and finally detected in the second detector. The difference of voltage of mirror 2 to source 1 was kept constant at a ratio value of 1.105. For MS/MS acquisitions Source 1 voltage was held at 8 kV and laser value was set 1000 units higher than in MS experiments. Precursor ions were selected for fragmentation by means of a Timed Ion Selector at a resolution value of 250 (full width at half maximum). Selected ions were decelerated before arrival to the collision chamber at the deceleration stack and were dissociated upon collisions with air at a kinetic energy of 1 keV (High-Energy Collision Induced Dissociation). Fragment ions were reaccelerated in the second source at 15 kV after a short delay time. The Metastable Suppressor was activated in all the MS/MS experiments to avoid the detection of the remaining precursor ions and unwanted metastable decay fragments. Data Explorer software was used for spectral treatment (smoothing and/or noise filtering). Only monoisotopic m/z ratios are reported. The mass spectrometer was externally calibrated with a peptide mixture provided by the manufacturer, covering the mass range of 900-4000 Da. When necessary, the instrument was calibrated with Insulin $(M+H^+=5730.609$ Da).

Figure 2A:
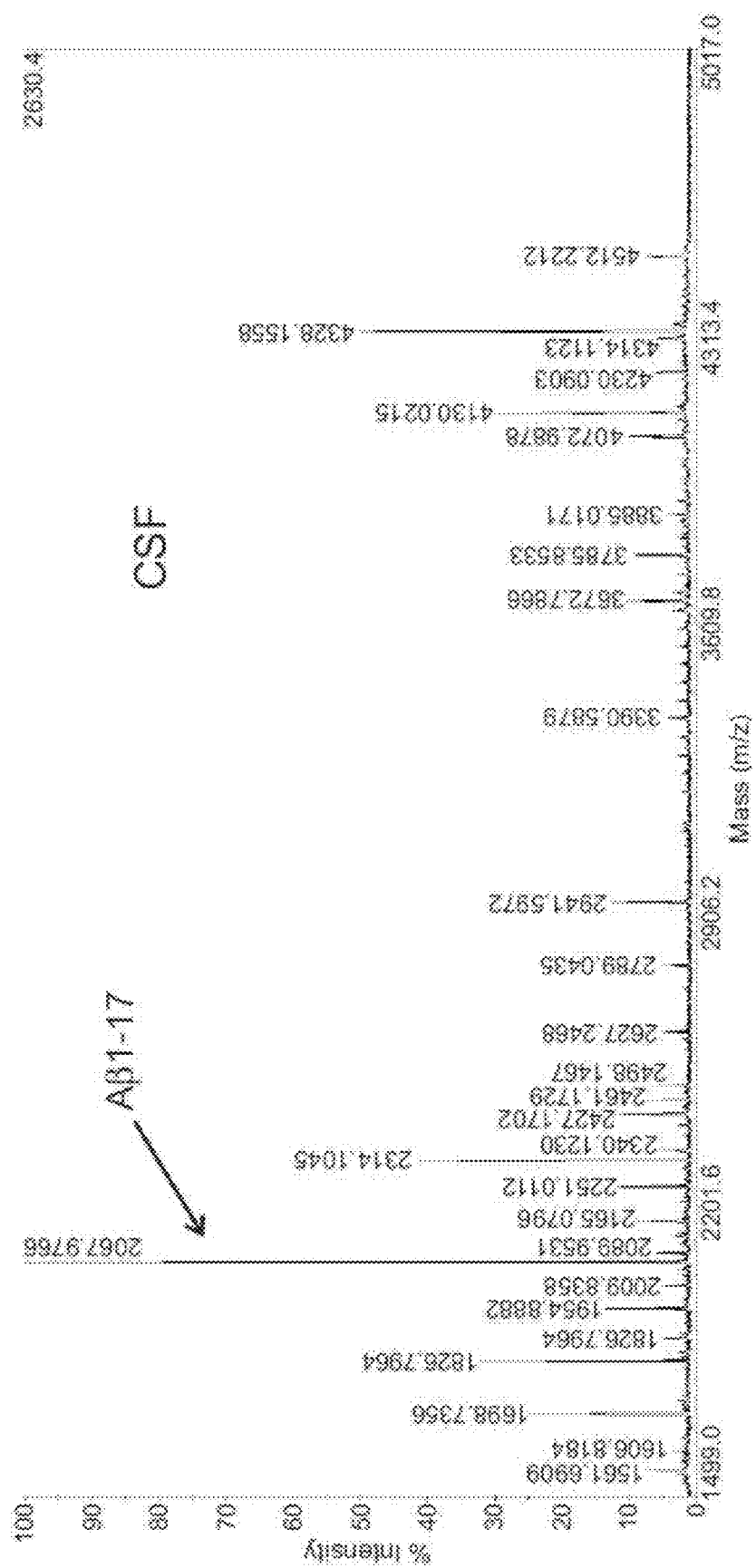
FIG. 2 shows the mass spectrometry analysis for a CSF sample (2A) and a plasma sample (2B), wherein the Aβ17 peak is indicated with an arrow.
Figure 2B:
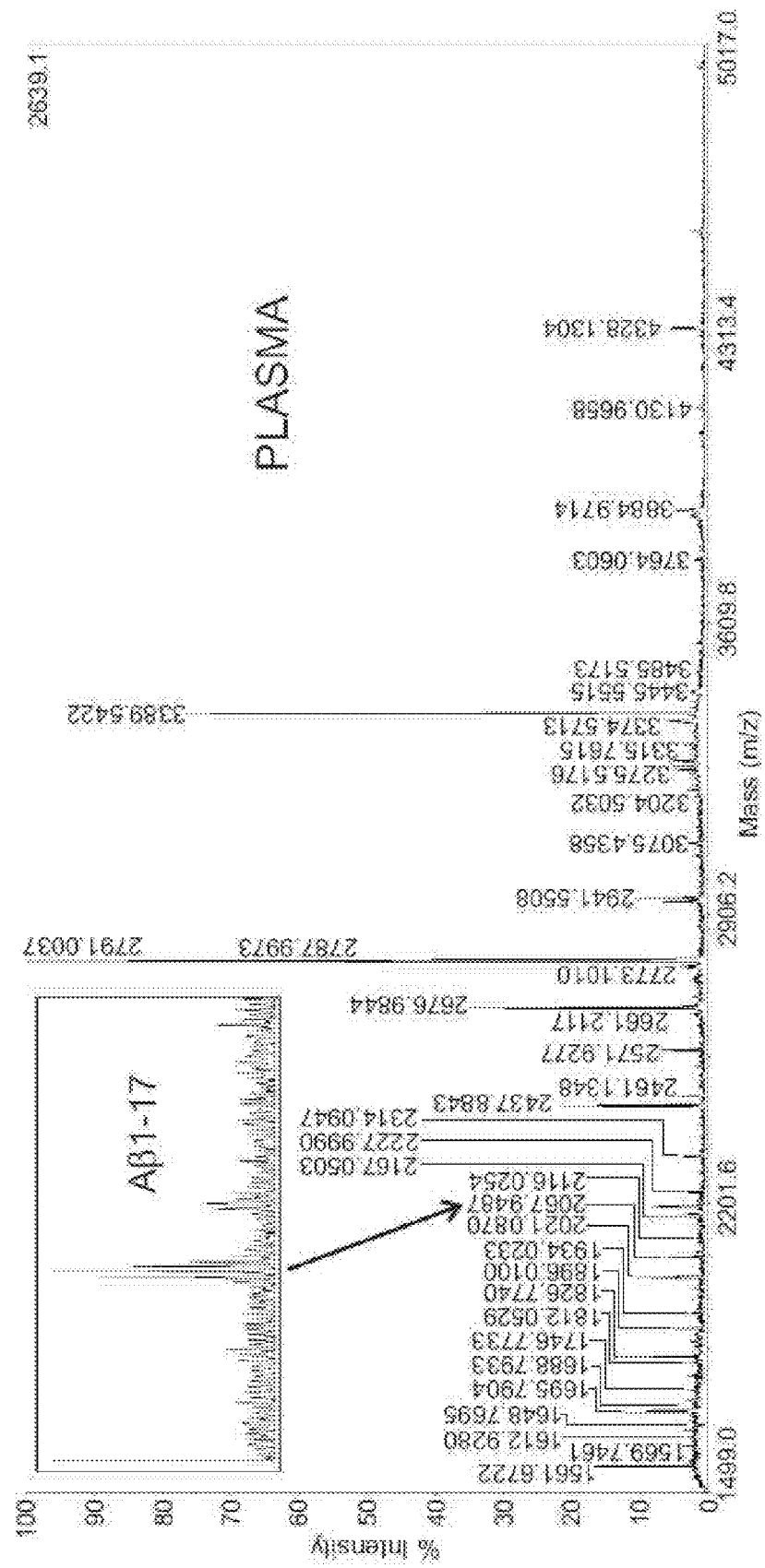

The results of the mass spectrometry are shown in FIG. 2, for a cerebrospinal fluid (CSF) sample and a plasma sample, wherein the peak corresponding to Aβ17 is indicated with an arrow.

(2) Determination by ELISA

Reagents and Solutions

- β-Amyloid 1-17 Standard, human origin. Stock solution of 20 ng/ml.
- Microplate optimized to adsorb antibodies to its surface.
- Capture monoclonal antibody specific to the $NH_2$ terminus of human Aβ peptide (6E10 antibody).
- Detection polyclonal antibody-biotin conjugated which specifically recognizes human Aβ peptides ending at amino acid 17.
- Amplifier solution of streptavidin-HRP conjugate.
- Stabilized chromogen TMB.
- Coating Buffer: 100 mM $Na_2CO_3/NaHCO_3$ pH 9.6.
- Washing Buffer: 50 mM Tris, 0.05% Tween20, 150 mM NaCl, pH 8.0.
- Blocking Buffer: 50 mM tris, 0.2% Tween20, 0.5% BSA, pH 8.0.
- Preservative Solution: 20 mg/ml trehalose, 50 mM tris, pH 8.0.
- Antibody Diluent: 50 mM tris, 0.05% BSA, 0.5M NaCl, 0.05% Tween20, pH 8.0.
- PBST: 80 mM $Na_2HPO_4$, 20 mM $NaH_2PO_4$, 100 mM NaCl, 0.5% Tween20, pH 7.5.
- Standard/Sample Diluent: synthetic blocking reagent 1:100 in PBST.
- Stop Solution: 1N $H_2SO_4$.

Method

The plate was coated using the 6E10 monoclonal capture antibody which recognises amino acids 1-17 in the Aβ amyloid peptide. The concentration used was determined according to the saturation concentration of the antibody, so that it will not be the limiting factor in the antigen-antibody reaction. For this purpose, the absorbance at 450 nm was related with the antibody concentration in each well by monitoring the antibody adsorbed to the well with an Anti-Mouse IgG HRP conjugated antibody incubated for 1 hour shaking at room temperature and an incubation step with the chromogen substrate followed by a stop of the reaction. The concentration at which the signal did not increase with the antibody concentration was chosen.

Once the saturation concentration has been selected, the microplates were coated with 100 μl of capture antibody in Coating Buffer and incubated overnight (ON) at 4° C. during approximately 20 h.

The plates were then washed 5 times with the Washing Buffer and 300 μl per well of Blocking Buffer was added. The plates were incubated for 3 hours at room temperature. The plates were then washed 5 times with the Washing Buffer and 100 μl of the Preservative Solution was added. The plates were left to evaporate until a white halo characteristic of trehalose appears (2-3 days at room temperature). The plates so treated could be kept at 4° C. covered with aluminium foil and are stable for two years.

Sample Preparation

Samples may be used undiluted or diluted 1:2 to 1:10 in Sample/Standard Diluent. Dilution 1:3 is recommended for plasma samples and 1:5 for blood cells samples. To ensure accurate quantification, the standard curves and blanks must be generated in the same diluents or buffers as the samples.

The samples of the standard curve of human Aβ17 (hAβ17) were prepared from a 200 pg/ml stock solution of the peptides Aβ17 on plates coated with the 6E10 mAb and treated with trehalose. From these solutions, serial dilutions 1:2 in Sample/Standard Diluent were made so as to give concentrations of 200, 100, 50, 25, 12.5, 6.25 and 3.125 pg/ml. 100 μl of each sample is added and incubated overnight at 4° C. (or for 2 h at 37° C.).

Detection Step

The detection antibody is a polyclonal biotin-conjugated antibody against human Aβ peptide ending at amino acid 17. The conjugation of the antibody to biotin takes place after an activation step and incubation overnight at room temperature in the dark. The biotin excess is inactivated in a further step. The detection antibody was added diluted in Antibody Diluent. 100 μl are added to each well and were then incubated for 1 h shaking at room temperature. Then, 100 μl of a 1/50 dilution in Antibody Diluent of HRP-coupled Streptavidin (from SIGMA) were added to each well and incubated for 1 h shaking at room temperature. For developing the plate, 100 μl of the chromogenic substrate TMB (ZEU Immunotec) were used. TMB was added and incubated in the dark during 45 minutes. 50 μl of stop solution was added per well. The absorbance at 450 nm was read in a plate reader Synergy HT (BioTek Instruments).

Aβ17 Quantification

The results may be calculated using any immunoassay software package. The method used to the curve fit is lineal regression and the concentration of Aβ17 was calculated as follows:

(i) Calculate the Average Net OD for each standard dilution and samples as follows: Average Net OD (nm)=Average Bound OD (nm)−Average Zero OD (nm).

(ii) On graph paper plot the Average Net OD of standard dilution (nm) against the concentration (pg/ml) of AB for the standards. Draw the best curve through these points to construct the standard curve.

(iii) The Aβ concentrations in unknown samples and controls can be determined by interpolation from the standard curve.

(iv) Multiply the values obtained for the samples by the dilution factor of each sample.

(v) Samples producing signals higher than the 200 pg/ml standard were further diluted and assayed.

Example 3

Reproducibility and Determination of the Detection and Quantification Limit

In order to analyse the reproducibility of the immunoassay, the intra-plate variability, the intra-assay variability, the inter-assay variability in plasma samples and the inter-assay variability in cell samples were measured.

The intra-plate variability was calculated by analysing the differences between the wells in triplicate, in samples, standard samples and reference samples in the same plate. In the intra-assay reproducibility, the concentration obtained for 4 reference plasma samples analysed in 11 different plates in the same assay was compared. In the inter-assay variability in plasma samples, the differences obtained in concentration when analysing two plasma samples in two different and independent assays were measured. The inter-assay variability in cell samples refers to the comparison of the Aβ17 levels between two different and independent determinations of 8 cell control samples.

The results obtained are shown in Table 1:

| | |
|---|---|
| Intra-plate variability (%) | 5.11 |
| Intra-assay variability (%) | 11.50 |
| Inter-assay variability plasma samples (%) | 9.51 |
| Inter-assay variability cell samples (%) | 21.55 |

The detection limit (DL) and quantification limit (QL) were calculated by two different methods:
(a) Method 1:

$$DL = \text{concentration}_{blank} + 3\sigma_{blank}$$

$$QL = \text{concentration}_{blank} + 10\sigma_{blank}$$

(b) Method 2:

$$DL = 3.3\sigma_{blank}/m$$

$$QL = 10\sigma_{blank}/m$$

wherein $\sigma_{blank}$ is the standard deviation of the blank and m is the slope of the calibration line The detection limit (DL) and quantification limit (QL) obtained using both methods are shown in Table 2:

| | Method 1 | Method 2 |
|---|---|---|
| Detection limit (pg/ml) | 21.883 | 2.914 |
| Quantification limit (pg/ml) | 21.904 | 8.830 |

Example 4

Correlation Between AD Diagnosis and Aβ17/Aβ40/Aβ42 Levels

Aβ17, Aβ40 and Aβ42 levels were determined using the ELISA sandwich assay described in Example 1 in plasma samples from a cohort of control healthy subjects (CS>65 or HC>65) older than 65 (19 subjects), from a cohort of subjects suffering from mild Alzheimer's disease (mild AD) (17 subjects), from a cohort of subjects having prodromal or probable mild cognitive impairment (MCI) (16 subjects) and from a cohort of subjects having non-prodromal or possible mild cognitive impairment (MCI) (16 subjects). The concentrations in pg/mL obtained for the peptides are shown in the Tables of FIG. 3A, FIG. 4A, FIG. 5A and FIG. 6A.

The Aβ17, Aβ40 and Aβ42 peptide levels in plasma (total peptide in plasma+peptide bound to cells) (PIB (137+40+42)) in mild AD differ significantly with regard to both control healthy subjects and MCI possible or non-prodromal subjects with respect to mild Alzheimer's disease subjects. However, the marker PIB (17+40+42) does not differ between HC>65 subjects and MCI probable, whereas PIB (40+42) do it with high significance (FIG. 3B).

Figure 3:
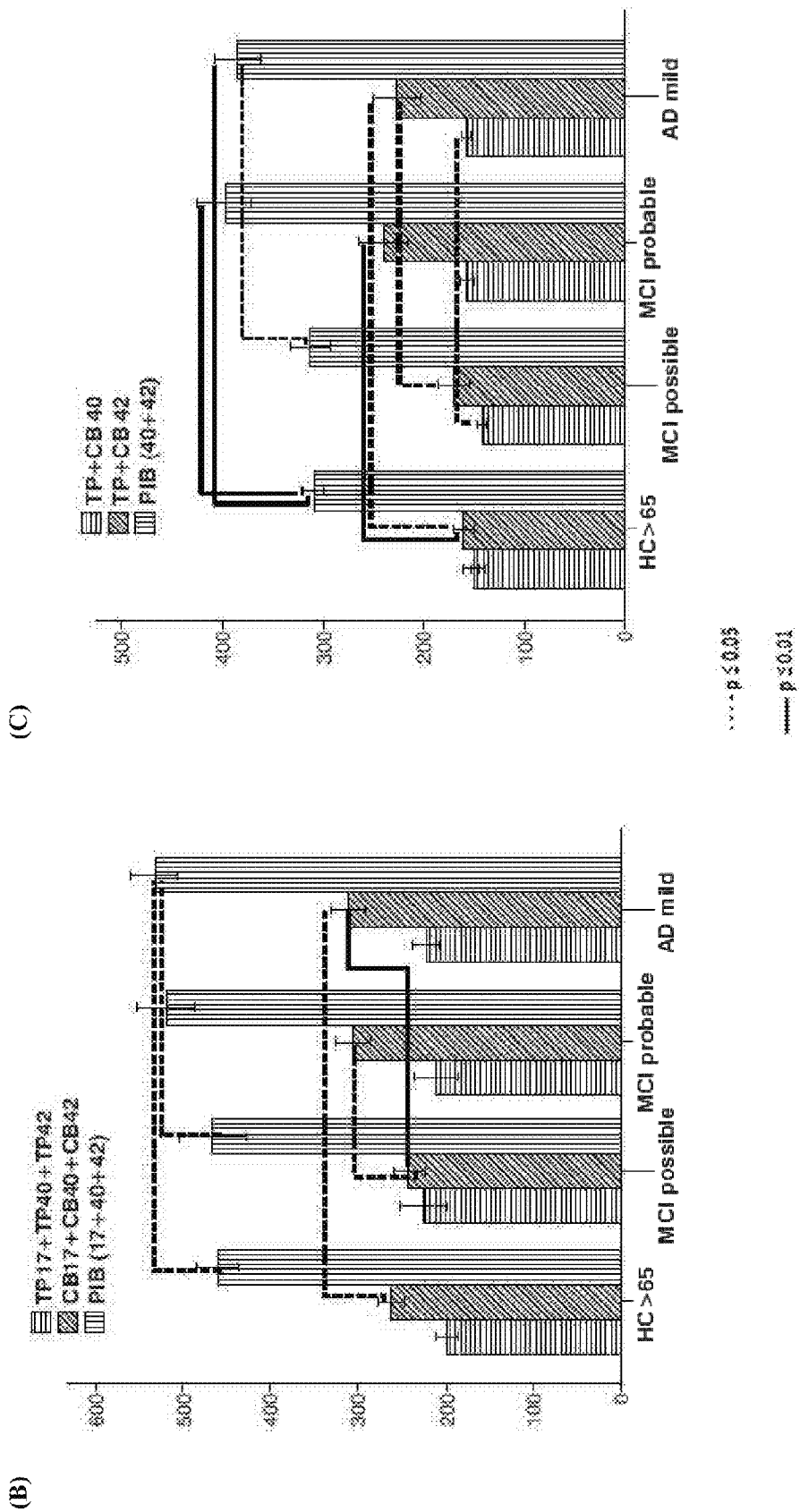
FIG. 3 shows the average values of some of the markers in different groups of patients. FP: free Aβ in plasma; TP: total Aβ in plasma; CB: Aβ bound to cells; PIB: pool in blood (total Aβ in plasma+Aβ bound to cells). (A) Concentration in pg/mL of the Aβ markers obtained in a sandwich ELISA for the different groups: CS>65 (healthy subjects older than 65), MCI possible (subjects with mild cognitive impairment with possible or non-prodromal AD), MCI probable (subjects with mild cognitive impairment with probable or prodromal AD) and AD mild (subjects with mild Alzheimer's disease). (B) and (C): Graphs representing the absorbance obtained in ELISA for several markers over the different groups.
Figure 4:
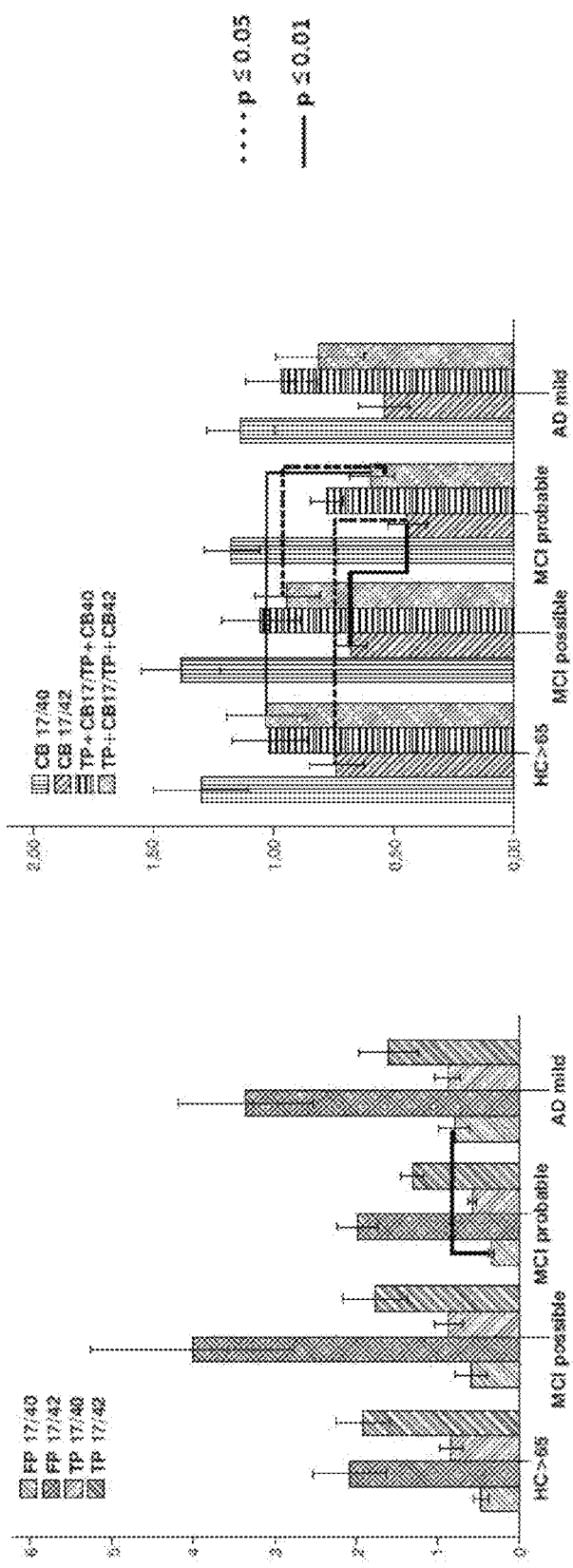
FIG. 4 shows the average values of some of the markers in different groups of patients. FP: free Aβ in plasma; TP: total Aβ in plasma; CB: Aβ bound to cells; PIB: pool in blood (total Aβ in plasma+Aβ bound to cells). (A) Ratios of the concentrations (in pg/mL) of the Aβ markers obtained in a sandwich ELISA for the different groups: CS>65 (healthy subject older than 65), MCI possible (mild cognitive impairment possible or non-prodromal), MCI probable (mild cognitive impairment probable or prodromal) and AD mild (mild Alzheimer's disease). (B) Graphs representing the absorbance obtained in ELISA for several markers over the different groups.
Figure 5:
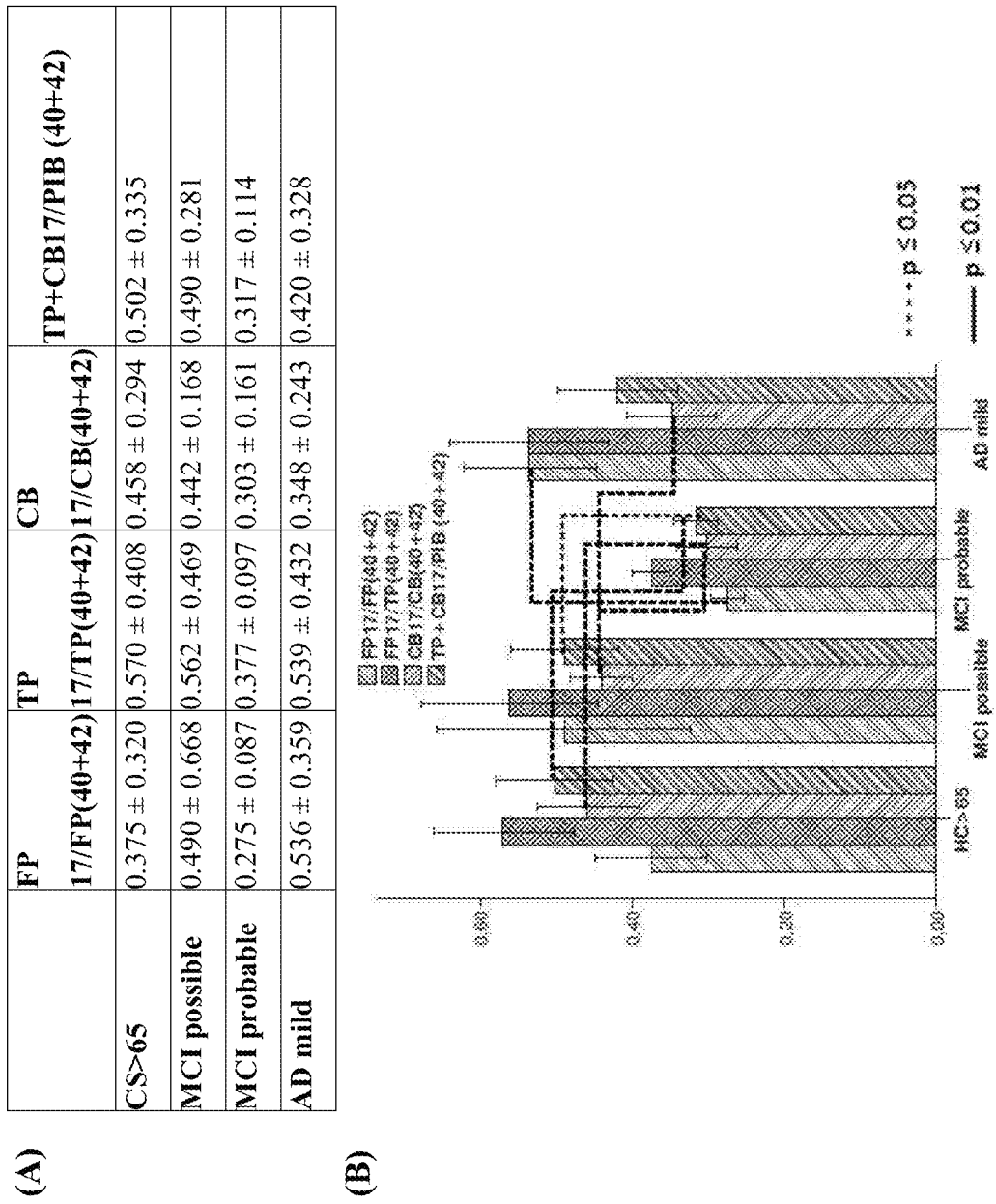
FIG. 5 shows the average values of some of the markers in different groups of patients. FP: free Aβ in plasma; TP: total Aβ in plasma; CB: Aβ bound to cells; PIB: pool in blood (total Aβ in plasma+Aβ bound to cells). (A) Ratios of the concentrations in pg/mL of the Aβ markers obtained in a sandwich ELISA for the different groups: CS>65 (healthy subject older than 65), MCI possible (mild cognitive impairment possible or non-prodromal), MCI probable (mild cognitive impairment probable or prodromal) and AD mild (mild Alzheimer's disease). (B) Graph representing the absorbance obtained in ELISA for several markers over the different groups.
Figure 6:
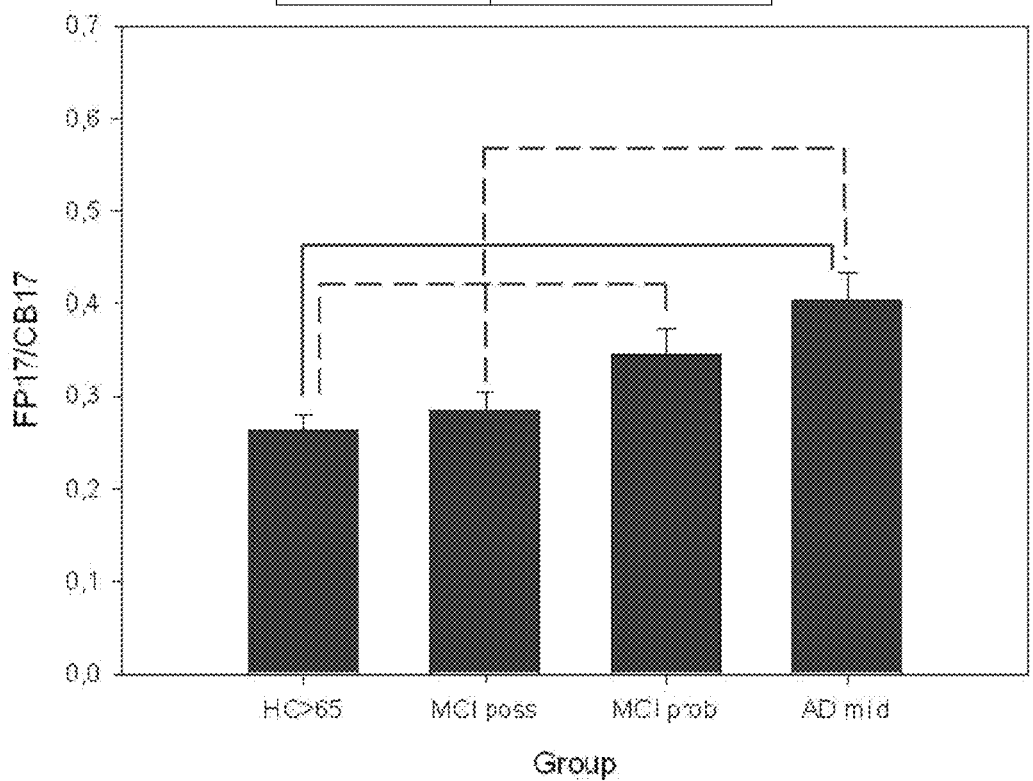
FIG. 6 shows the ratio between free Aβ17 in plasma (FP) and Aβ17 bound to cells (CB) for the distinction between the different groups. (A) concentration in pg/mL of the Aβ markers obtained in a sandwich ELISA for the different groups: CS>65 (healthy subject older than 65), MCI possible (mild cognitive impairment possible or non-prodromal), MCI probable (mild cognitive impairment probable or prodromal) and AD mild (mild Alzheimer's disease). (B) Graph representing the absorbance obtained in ELISA for said marker over the different groups.

Other relevant parameters to be measured, which are able to distinguish between groups, are the following (FIGS. 3, 4, 5 and 6):
The Aβ17, Aβ40 and Aβ42 peptide levels bound to cells (CB (17+40+42)). As shown in FIG. 3, the levels of these peptides bound to cells are higher in MCI probable and mild AD subjects than in MCI possible and healthy subjects. And it is possible to distinguish with high significance between healthy subjects and mild AD, MCI possible and MCI probable and between MCI possible and mild AD.
The total Aβ42 total peptide levels in plasma+Aβ42 peptide levels bound to cells (TP42+CB42). As shown in FIG. 3, the levels of these markers are higher in MCI probable and mild AD subjects than in MCI possible and healthy subjects. And it is possible to distinguish with high significance between healthy subjects and mild AD or MCI probable and between MCI possible and mild AD.
The total Aβ40 total peptide levels in plasma added to the Aβ40 peptide levels bound to cells (TP40+CB40). As shown in FIG. 3, the levels of these markers are higher in MCI probable and mild AD subjects than in MCI possible and healthy subjects. And it is possible to distinguish with high significance between MCI possible and mild AD.
The ratio between Aβ17 peptide levels free in plasma and Aβ40 peptide levels free in plasma (FP17/40) is able to distinguish between MCI probable and mild AD (FIG. 4).
The ratio between Aβ17 peptide levels bound to cells and Aβ42 peptide levels bound to cells (CB17/42) is able to distinguish between healthy subjects or MCI possible subjects and MCI probable (FIG. 4).
The ratio between total Aβ17 peptide levels in plasma+Aβ17 peptide levels bound to cells and total Aβ42 peptide levels in plasma added to the Aβ42 peptide levels bound to cells (TP17+CB17/TP42+CB42) is able to distinguish between healthy subjects or MCI possible subjects and MCI probable (FIG. 4).
The ratio between Aβ17 peptide levels free in plasma and Aβ40 and Aβ42 peptides levels free in plasma (FP17/FP40+FP42) is able to distinguish between MCI probable and mild AD (FIG. 5).
The ratio between Aβ17 peptide levels bound to cells and Aβ40 and Aβ42 peptide levels bound to cells (CB17/CB40+CB42) is able to distinguish between healthy subjects or MCI possible subjects and MCI probable and between healthy subjects and mild AD (FIG. 5).
The ratio between total Aβ17 peptide levels in plasma+Aβ17 peptide levels bound to cells and the total Aβ40 and Aβ42 peptide levels in plasma (PIB (40+42)) is able to distinguish between healthy subjects or MCI possible subjects from MCI probable (FIG. 5).
The ratio between Aβ17 peptide levels free in plasma and Aβ17 peptide levels bound to cells (FP17/CB17) is able to distinguish between healthy subjects or MCI possible subjects from mild AD and between healthy subjects and MCI probable (FIG. 6). The statistical analysis (U Mann-Whitney test) with all the Aβ17 ratios shows statistically significant differences only with the marker Aβ17 peptide levels free in plasma/Aβ17 peptide levels bound to cells (FP17/CB17) (see Table 3).
Likewise, there is a relationship between the ratio Aβ17 peptide levels free in plasma and Aβ17 peptide levels bound to cells with the evolution of the AD. The more advanced the cognitive impairment is, the higher is the level of Aβ17 peptide free in plasma is and thus, the higher is also the ratio Aβ17 peptide levels free in plasma and Aβ17 peptide levels bound to cells (FP17/CB17).

TABLE 3

| | FP17/TP17 | TP17/CB17 | FP17/CB17 | FP17/PIB17 | TP17/PIB17 | CB17/PIB17 |
|---|---|---|---|---|---|---|
| HC > 65 vs MCI poss. | 0.313 | 0.987 | 0.296 | 0.282 | 0.987 | 0.987 |
| HC > 65 vs MCI prob. | 0.169 | 0.608 | 0.020 | 0.082 | 0.608 | 0.608 |
| HC > 65 vs ADm. | 0.113 | 0.296 | <0.001 | 0.004 | 0.296 | 0.296 |
| MCI poss vs MCI prob. | 0.749 | 0.720 | 0.109 | 0.462 | 0.720 | 0.720 |
| MCI poss vs ADmild | 0.615 | 0.397 | 0.002 | 0.075 | 0.397 | 0.397 |
| MCI prob vs ADmild. | 0.815 | 0.439 | 0.228 | 0.288 | 0.439 | 0.439 |

The invention claimed is:

1. An antibody that specifically binds to amyloid-beta (Aβ) (1-17) peptide, wherein the antibody does not show substantial cross-reactivity with an Aβ peptide selected from the group consisting of Aβ(1-15), Aβ(1-16), Aβ(1-38), Aβ(1-40), Aβ(1-42), and combinations thereof.

2. The antibody of claim 1, wherein the antibody is polyclonal.

3. The antibody of claim 1, wherein the antibody is monoclonal.

4. A kit for the detection of Aβ(1-17) peptide, comprising:
(i) the antibody of claim 1 and
(ii) a second antibody that is not the first antibody.

5. The kit of claim 2, wherein the first or second antibody is coupled to a first member of a binding pair selected from the group consisting of hapten-antibody, antigen-antibody, biotin-avidin, biotin analogue-avidin, biotin-streptavidin, biotin analogue-streptavidin, sugar-lectin, enzyme-cofactor, folic acid-folate, double stranded oligonucleotides that selectively bind to proteins-transcription factors, nucleic acid-complementary nucleic acid, nucleic acid analogue-complementary nucleic acid, and receptor-ligand.

6. The kit of claim 5, further comprising a second member of said binding pair, wherein said second member is coupled to a detectable tag.

7. A method for determining or detecting Aβ(1-17) peptide in a sample comprising the steps of: (i) capturing the Aβ(1-17) present in the sample with a first antibody which binds specifically to said peptide to form first complexes, (ii) contacting the first complexes formed in step (i) with a second antibody to form second complexes, wherein said second antibody is the antibody of claim 1, and wherein said second antibody is different than the first antibody and is coupled to a first member of a binding pair selected from the group consisting of hapten-antibody, antigen-antibody, biotin-avidin, biotin analogue-avidin, biotin-streptavidin, biotin analogue-streptavidin, sugar-lectin, enzyme-cofactor, folic acid-folate, double stranded oligonucleotides that selectively bind to proteins-transcription factors, nucleic acid-complementary nucleic acid, nucleic acid analogue-complementary nucleic acid, and receptor-ligand (iii) contacting the second complexes formed in step (ii) with the second member of the binding pair, which is coupled to a detectable tag, and (iv) detecting or determining the activity or amount of the detectable tag.

8. The method of claim 7, wherein the sample is selected from the group consisting of blood, serum, plasma and CSF.

* * * * *

UNITED STATES PATENT AND TRADEMARK OFFICE
CERTIFICATE OF CORRECTION

PATENT NO. : 9,255,932 B2  
APPLICATION NO. : 14/004634  
DATED : February 9, 2016  
INVENTOR(S) : Manuel Sarasa Barrio Page 1 of 1

It is certified that error appears in the above-identified patent and that said Letters Patent is hereby corrected as shown below:

On the title page item [73], Assignee: "Aracion Biotech, S.L." should read --Araclon Biotech, S.L.--.

In the Claims

At column 49, line 24 of the Letters Patent, in claim 5 (original claim 3), "The kit of claim 2" should read --The kit of claim 4--.

Signed and Sealed this  
Third Day of May, 2016

Michelle K. Lee  
*Director of the United States Patent and Trademark Office*

SEQUENCE LISTING

<160> NUMBER OF SEQ ID NOS: 6

<210> SEQ ID NO 1
<211> LENGTH: 17
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu

<210> SEQ ID NO 2
<211> LENGTH: 6
<212> TYPE: PRT
<213> ORGANISM: Artificial sequence
<220> FEATURE:
<223> OTHER INFORMATION: Peptide used to prepare the anti-Abeta17-
      specific polyclonal Ab

<400> SEQUENCE: 2

Val His His Gln Lys Leu
1               5

<210> SEQ ID NO 3
<211> LENGTH: 7
<212> TYPE: PRT
<213> ORGANISM: Artificial sequence
<220> FEATURE:
<223> OTHER INFORMATION: Peptide used to prepare the anti-Abeta17-
      specific polyclonal Ab

<400> SEQUENCE: 3

Glu Val His His Gln Lys Leu
1               5

<210> SEQ ID NO 4
<211> LENGTH: 770
<212> TYPE: PRT
<213> ORGANISM: Homo sapiens

<400> SEQUENCE: 4

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

```
Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495
```

```
Tyr Val Arg Ala Glu Gln Lys Asp Arg Gln His Thr Leu Lys His Phe
                500                 505                 510
Glu His Val Arg Met Val Asp Pro Lys Lys Ala Ala Gln Ile Arg Ser
            515                 520                 525
Gln Val Met Thr His Leu Arg Val Ile Tyr Glu Arg Met Asn Gln Ser
        530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                565                 570                 575
Leu Ala Asn Met Ile Ser Glu Pro Arg Ile Ser Tyr Gly Asn Asp Ala
            580                 585                 590
Leu Met Pro Ser Leu Thr Glu Thr Lys Thr Thr Val Glu Leu Leu Pro
        595                 600                 605
Val Asn Gly Glu Phe Ser Leu Asp Asp Leu Gln Pro Trp His Ser Phe
610                 615                 620
Gly Ala Asp Ser Val Pro Ala Asn Thr Glu Asn Glu Val Glu Pro Val
625                 630                 635                 640
Asp Ala Arg Pro Ala Ala Asp Arg Gly Leu Thr Thr Arg Pro Gly Ser
                645                 650                 655
Gly Leu Thr Asn Ile Lys Thr Glu Glu Ile Ser Glu Val Lys Met Asp
            660                 665                 670
Ala Glu Phe Arg His Asp Ser Gly Tyr Glu Val His His Gln Lys Leu
        675                 680                 685
Val Phe Phe Ala Glu Asp Val Gly Ser Asn Lys Gly Ala Ile Ile Gly
        690                 695                 700
Leu Met Val Gly Gly Val Val Ile Ala Thr Val Ile Val Ile Thr Leu
705                 710                 715                 720
Val Met Leu Lys Lys Lys Gln Tyr Thr Ser Ile His His Gly Val Val
                725                 730                 735
Glu Val Asp Ala Ala Val Thr Pro Glu Glu Arg His Leu Ser Lys Met
            740                 745                 750
Gln Gln Asn Gly Tyr Glu Asn Pro Thr Tyr Lys Phe Phe Glu Gln Met
        755                 760                 765
Gln Asn
    770

<210> SEQ ID NO 5
<211> LENGTH: 42
<212> TYPE: PRT
<213> ORGANISM: Homo sapiens

<400> SEQUENCE: 5

Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Ile Ile
            20                  25                  30
Gly Leu Met Val Gly Gly Val Val Ile Ala
        35                  40

<210> SEQ ID NO 6
<211> LENGTH: 40
<212> TYPE: PRT
<213> ORGANISM: Homo sapiens

<400> SEQUENCE: 6
```

-continued

```
Asp Ala Glu Phe Arg His Asp Ser Gly Tyr Glu Val His His Gln Lys
1               5               10                  15

Leu Val Phe Phe Ala Glu Asp Val Gly Ser Asn Lys Gly Ala Ile Ile
            20              25              30

Gly Leu Met Val Gly Gly Val Val
        35              40
```